US012800573B2

(12) United States Patent
Ishii et al.

(10) Patent No.: US 12,800,573 B2
(45) Date of Patent: Nov. 17, 2026

(54) METHOD FOR PRODUCING BRAIN ORGANOID INCLUDING AGGREGATED TAU PROTEIN

(71) Applicant: KEIO UNIVERSITY, Tokyo (JP)

(72) Inventors: Hiroko Ishii, Tokyo (JP); Hideyuki Okano, Tokyo (JP); Takahiro Kondo, Tokyo (JP); Yuta Sato, Yokohama (JP)

(73) Assignee: KEIO UNIVERSITY, Tokyo (JP)

( * ) Notice: Subject to any disclaimer, the term of this patent is extended or adjusted under 35 U.S.C. 154(b) by 311 days.

(21) Appl. No.: 18/550,496

(22) PCT Filed: Mar. 18, 2022

(86) PCT No.: PCT/JP2022/012502
§ 371 (c)(1),
(2) Date: Sep. 14, 2023

(87) PCT Pub. No.: WO2022/196793
PCT Pub. Date: Sep. 22, 2022

(65) Prior Publication Data

US 2024/0151712 A1 May 9, 2024

(30) Foreign Application Priority Data

Mar. 19, 2021 (JP) ................................ 2021-046480

(51) Int. Cl.
*G01N 33/50* (2006.01)
*C12N 5/071* (2010.01)
*C12N 15/86* (2006.01)

(52) U.S. Cl.
CPC ....... *G01N 33/5082* (2013.01); *C12N 5/0697* (2013.01); *C12N 15/86* (2013.01);
(Continued)

(58) Field of Classification Search
None
See application file for complete search history.

(56) References Cited

U.S. PATENT DOCUMENTS

2021/0040445 A1 2/2021 Nakamura et al.
2022/0356443 A1 11/2022 Ishii et al.

FOREIGN PATENT DOCUMENTS

CN 110679549 A 1/2020
JP 2021-023228 2/2021
(Continued)

OTHER PUBLICATIONS

Jaworski, Tomasz; et al; "AAV-Tau Mediates Pyramidal Neurodegeneration by Cell-Cycle Re-Entry without Neurofibrillary Tangle Formation in Wild-Type Mice" PLoS One, 4, e7280, 2009 (Year: 2009).*
(Continued)

*Primary Examiner* — David W Berke-Schlessel
(74) *Attorney, Agent, or Firm* — Barnes & Thornburg LLP

(57) ABSTRACT

A method for producing a brain organoid having an aggregated tau protein including (a) culturing pluripotent stem cells in the presence of a SMAD inhibitor to form an embryoid body, (b) embedding the embryoid body in an extracellular matrix and three-dimensionally culturing the embryoid body in the presence of a SMAD inhibitor and a GSK3β inhibitor to form an organoid that includes neural precursor cells, (c) extracting the organoid from the extracellular matrix and suspension-culturing the organoid in the presence of LIF to form a brain organoid, (d) forcing the brain organoid to express a mutant MAPT gene, and (e) further suspension-culturing the brain organoid after (d) to obtain a brain organoid having an aggregated tau protein.

10 Claims, 17 Drawing Sheets

Specification includes a Sequence Listing.

(52) U.S. Cl.
CPC .... *G01N 33/5038* (2013.01); *C12N 2501/115* (2013.01); *C12N 2501/235* (2013.01); *C12N 2501/727* (2013.01); *C12N 2503/04* (2013.01); *C12N 2513/00* (2013.01); *C12N 2750/14143* (2013.01)

(56) References Cited

FOREIGN PATENT DOCUMENTS

| | | |
|---|---|---|
| WO | WO2021/006107 | 1/2021 |
| WO | WO2021/090877 | 5/2021 |

OTHER PUBLICATIONS

Klein, Ronald L; "Tau expression levels from various adeno-associated virus vector serotypes produce graded neurodegenerative disease states" European Journal of Neuroscience, 27, 1615-1625, 2008 (Year: 2008).*
Choi, Se Hoon, et al., "A Three-Dimensional Human Neural Cell Culture Model of Alzheimer's Disease," 2014, Nature, vol. 515, No. 7526, pp. 274-278.
Matsumoto, Gen, et al., "Tau Fibril Formation in Cultured Cells Compatible with a Mouse Model of Tauopathy," 2018, Int. J. Mol. Sci., vol. 19, No. 1497, pp. 1-14.
Lines, G. et al., "Modelling Frontotemporal Dementia Using Patientderived Induced Pluripotent Stem Cells," 2020, Mol. Cell Neurosci., vol. 109, No. 103553, pp. 1-23.
Nakamura, M., et al., "Pathological Progression Induced by the Frontotemporal Dementia-Associated R406W Tau Mutation in Patient-Derived iPSCs," Stem Cell Reports, 2019, vol. 13, No. 4, pp. 684-699.
Shimozawa, Akinori et al., "Construction of a Tau Accumulation Model by Overexpression of P301L Mutant Human Tau Using Adenoassociated Virus (AAV)," 2021, Programs and Abstracts of the 40th Annual Meeting of Japan Society for Dementia Research, p. 303.
Venkataraman, L., et al., "Modeling Neurodegenerative Diseases with Cerebral Organoids and Other Three-Dimensional Culture Systems: Focus on Alzheimer's Disease," 2022, Stem Cell Reviews and Reports, No. 18, pp. 696-717.
Fischer, J., et al., "Genetic Modification of Brain Organoids", 2019, Frontiers in Cellular Neuroscience, vol. 13, Article 558, pp. 1-9.
Adams, J. W., et al., "Brain Organoids as Tools for Modeling Human Neurodevelopmental Disorders," 2019, Physiology, No. 34, pp. 365-375.
Seo, J., et al., "Inhibition of p25/Cdk5 Attenuates Tauopathy in Mouse and iPSC Models of Frontotemporal Dementia," 2017, The Journal of Neuroscience, No. 37, pp. 9917-9924.
PCT International Search Report prepared for PCT/JP2022/012502, completed May 24, 2022 and English Translation.
PCT International Preliminary Report on Patentability prepared for PCT/JP2022/012502, completed Apr. 18, 2023 and English Translation.
Waseem K. Raja et al: "Self-Organizing 3D Human Neural Tissue Derived from Induced Pluripotent Stem Cells Recapitulate Alzheimer's Disease Phenotypes", Plos One, vol. 11, No. 9, 2016, pp. 1-18.
Lewis J et al: "Neurofibrillary Tangles, Amyotrophy and Progressive Motor Disturbance in Mice Expressing Mutant (P301L) Tau Protein", Nature Genetics, Nature Publishing Group US, New York, vol. 25, No. 4, Aug. 1, 2000, pp. 402-405.
Qian Xuyu et al: "Brain-Region-Specific Organoids Using Mini-bioreactors for Modeling ZIKV Exposure", Cell, Elsevier, Amsterdam NL, vol. 165, No. 5, 2016, pp. 1238-1254.
Gonzalez Cesar et al: "Modeling amyloid beta and tau pathology in human cerebral organoids", Molecular Psychiatry, Nature Publishing Group UK, London, vol. 23, No. 12, Aug. 31, 2018, pp. 2363-2374.
Shimada Hiroko et al: "A next-generation iPSC-derived forebrain organoid model of taupathology with tau fibrils by AAV-mediated gene transfer", Cell Reports Methods, vol. 2, No. 9, Sep. 1, 2022, p. 100289.
Supplementary European Search Report and European Search Opinion prepared for Application No. 22771538.0, mailed Apr. 1, 2025.
Ma Denglei, et al., "Establishment and characterization of microtubule-associated protein tau over-expression cell and transgenic animal models", Journal of Capital Medical University, vol. 40, Issue (4), 2019, pp. 582-587.
Office Action prepared for Chinese Application No. 202280021199.9, mailed Aug. 14, 2026.

* cited by examiner

SEQUENCE LISTING

<160> NUMBER OF SEQ ID NOS: 2

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1 5 10 15

Thr Tyr Gly Leu Gly Asp Arg Lys Asp Gln Gly Gly Tyr Thr Met His

-continued

```
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Leu Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```

```
<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Ser Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
```

-continued

```
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```

METHOD FOR PRODUCING BRAIN ORGANOID INCLUDING AGGREGATED TAU PROTEIN

CROSS-REFERENCE TO RELATED APPLICATIONS

This application is a national stage entry under 35 U.S.C. § 371 (b) of PCT International Application No. PCT/JP2022/012502, filed Mar. 18, 2022, which claims the benefit of Japanese Patent Application Serial No. 2021-046480, filed Mar. 19, 2021, the entire disclosures of both of which are incorporated herein by reference.

TECHNICAL FIELD

The present invention relates to a method for producing a brain organoid having an aggregated tau protein. In more detail, the present invention relates to a method for producing a brain organoid having an aggregated tau protein, a brain organoid, and a method for screening prophylactic or therapeutic agents for tauopathy. Priority is claimed on Japanese Patent Application No. 2021-046480, filed Mar. 19, 2021, the content of which is incorporated herein by reference.

BACKGROUND ART

Organoids are small organs formed by the accumulation of cells and have a structure and functions which are similar to organs in vivo. In recent years, research has been actively conducted on the production of various organoids from pluripotent stem cells, for example, producing brain organoids, intestinal organoids, liver organoids, kidney organoids, and the like.

As a pathology, neurodegenerative diseases in which fibrotic tau protein inclusions are observed in neurons and glial cells are collectively called tauopathies. Tauopathies include Alzheimer's disease, progressive supranuclear palsy, corticobasal degeneration, Pick's disease, and the like. It is known that abnormal intracellular accumulation of phosphorylated tau protein is found in the brains of patients with tauopathy.

Alzheimer's disease model mice have been developed for the development of therapeutic agents for Alzheimer's disease. However, the brain structures of humans and mice are different and findings obtained using Alzheimer's disease model mice may not be applicable to humans. Therefore, there is a demand for an experiment system which is usable in vitro and able to reproduce the pathophysiology of Alzheimer's disease more faithfully.

For example, Patent Document 1 describes the production of brain organoids having amyloid plaques from iPS cells derived from Alzheimer's disease patients. In addition, Non-Patent Documents 1 and 2 describe tau aggregation model cells.

CITATION LIST

Patent Document

[Patent Document 1]
PCT International Publication No. WO2021/006107

Non Patent Documents

[Non Patent Document 1]
Choi S. H., et al, A three-dimensional human neural cell culture model of Alzheimer's disease, Nature, 515 (7526), 274-278, 2014

[Non Patent Document 2]
Matsumoto G., et al., Tau Fibril Formation in Cultured Cells Compatible with a Mouse Model of Tauopathy, Int. J. Mol. Sci., 19, 1497, 2018

SUMMARY OF INVENTION

Technical Problem

However, there are no known brain organoids that are usable as tau aggregation models. Therefore, an object of the present invention is to provide a technique for efficiently producing a brain organoid having an aggregated tau protein.

Solution to Problem

The present invention includes the following aspects.

[1] A method for producing a brain organoid having an aggregated tau protein, the method including a step (a) of culturing pluripotent stein cells in the presence of a SMAD inhibitor to form an embryoid body, a step (b) of embedding the embryoid body in an extracellular matrix and three-dimensionally culturing the embryoid body in the presence of a SMAD inhibitor and a glycogen synthase kinase 3β (GSK3β) inhibitor to form an organoid that includes neural precursor cells, a step (c) of extracting the organoid from the extracellular matrix and suspension-culturing the organoid in the presence of leukemia inhibitory factor (LIF) to form a brain organoid, a step (d) of forcing the brain organoid to express a mutant microtubule associated protein tau (MAPT) gene, and a step (e) of further suspension-culturing the brain organoid after step (d) to obtain a brain organoid having an aggregated tau protein.

[2] The method for producing a brain organoid according to [1], in which the mutant MAPT gene is a gene encoding a tau protein having a P301L mutation.

[3] The method for producing a brain organoid according to [1] or [2], in which forced expression of the mutant MAPT gene is performed by gene transfer using an adeno-associated virus (AAV).

[4] The method for producing a brain organoid according to [3], in which the forced expression of the mutant MAPT gene is performed by injecting the AAV into the brain organoid.

[5] The production method according to any of [1] to [4], in which at least a part of step (c) is performed in the presence of more than 20% by volume of oxygen.

[6] The production method according to any of [1] to [5], in which step (c) is performed for 3 weeks or longer.

[7] The production method according to any of [1] to [6], in which step (e) is performed for 5 weeks or longer.

[8] The production method according to any of [1] to [7], further including a step for culturing the pluripotent stem cells in the presence of less than 100 ng/mL of fibroblast growth factor-2 (FGF2) before step (a).

[9] The production method according to any of [1] to [8], in which the pluripotent stem cells are cultured feeder-free.

[10] A brain organoid, in which, in a cross-section, an average ratio of an area of a region where a phosphorylated tau protein is present is 2% or more with respect to a total area of the cross-section, or, in a cross-section, an average ratio of an area of a region where an aggregated tau protein is present is 1% or more with respect to a total area of the cross-section.

[11] A method for screening for a therapeutic agent for tauopathy, the method including a step for culturing the brain organoid according to in the presence of a test substance, and a step for measuring an amount of a phosphorylated tau protein present or an amount of an aggregated tau protein present in the brain organoid, in which a decrease in the amount of the phosphorylated tau protein present or the amount of the aggregated tau protein present, compared to in the absence of the test substance, indicates that the test substance is a therapeutic agent for tauopathy.

[12] A method for screening prophylactic or therapeutic agents for tauopathy, the method including a step (a) of culturing pluripotent stem cells in the presence of a SMAD inhibitor to form an embryoid body, a step (b) of embedding the embryoid body in an extracellular matrix and three-dimensionally culturing the embryoid body in the presence of a SMAD inhibitor and a GSK3β inhibitor to form an organoid that includes neural precursor cells, a step (c) of extracting the organoid from the extracellular matrix and suspension-culturing the organoid in the presence of LIE to form a brain organoid, a step (d) of forcing the brain organoid to express a mutant MAPT gene, a step (e) of further suspension-culturing the brain organoid for 5 weeks or longer after step (d), and a step (f) of measuring an amount of a phosphorylated tau protein present or an amount of an aggregated tau protein present in the brain organoid during step (e) or after step (e), in which at least a part of steps (c) to (e) is performed in the presence of a test substance and a decrease in the amount of the phosphorylated tau protein present or the amount of the aggregated tau protein present, as measured in step (f), compared to in the absence of the test substance, indicates that the test substance is a prophylactic or therapeutic agent for tauopathy.

Advantageous Effects of Invention

The present invention provides a technique for efficiently producing a brain organoid having an aggregated tau protein.

DESCRIPTION OF EMBODIMENTS

Figure 1:
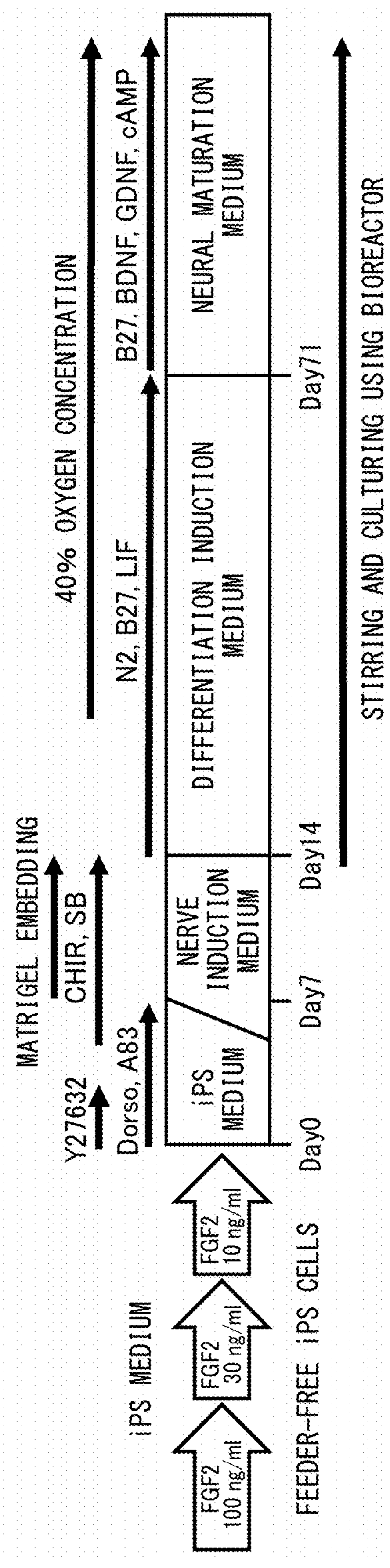
FIG. 1 is a diagram showing the schedule of brain organoid production in Experimental Example 1.

[Method for Producing Brain Organoid Having Aggregated Tau Protein]

In one embodiment, the present invention provides a method for producing a brain organoid having an aggregated tau protein, the method including a step (a) of culturing pluripotent stem cells in the presence of a SMAD inhibitor to form an embryoid body, a step (b) of embedding the embryoid body in an extracellular matrix and three-dimensionally culturing the embryoid body in the presence of a SMAD inhibitor and a GSK3β inhibitor to form an organoid that includes neural precursor cells, a step (c) of extracting the organoid from the extracellular matrix and suspension-culturing the organoid in the presence of LIF to form a brain organoid, a step (d) of forcing the brain organoid to express a mutant MAPT gene, and a step (e) of further suspension-culturing the brain organoid after step (d) to obtain a brain organoid having an aggregated tau protein.

As described below in the Examples, the production method of the present embodiment makes it possible to efficiently produce a brain organoid having an aggregated tau protein.

In the present specification, examples of pluripotent stem cells include embryonic stem cells (ES cells), induced pluripotent stem cells (iPS cells), and the like. The pluripotent stem cells are preferably human cells. In addition, the pluripotent stem cells may be wild-type cells, cells having mutations in Alzheimer's disease-related genes, or cells having the ApoE4/4 isoform which is an Alzheimer's disease risk factor.

Examples of Alzheimer's disease-related genes include the presenilin 1 (PS1) gene, the presenilin 2 (PS2) gene, the β-amyloid precursor protein (APP) gene, and the like.

The NCBI accession number for the genomic DNA of the human PS1 gene is NC_000014.9. The NCBI accession number for the genomic DNA of the human PS2 gene is NC_000001.11. The NCBI accession number for the genomic DNA of the human APP gene is NC_000021.9. The NCBI accession number for the genomic DNA of the human APOE gene is NC_000019.10.

Examples of pluripotent stem cells having mutations in Alzheimer's disease-related genes include pluripotent stem cells having mutations in these Alzheimer's disease-related genes that lead to the onset of Alzheimer's disease.

Examples of mutations that lead to the onset of Alzheimer's disease include a genetic mutation in the PS1 gene that causes an amino acid mutation (A246E) from alanine to glutamic acid at the 246th amino acid of the PS1 protein, a genetic mutation in the PS2 gene that causes an amino acid mutation (N141I) from asparagine to isoleucine in the 141st amino acid of the PS2 protein, a duplication of the APP gene, and the like, without being limited thereto.

Mutations or isoforms that lead to the onset of Alzheimer's disease may be mutations or isoforms artificially introduced by genome editing or the like. Alternatively, pluripotent stem cells produced from cells derived from Alzheimer's disease patients may be used as pluripotent stem cells having mutations in Alzheimer's disease-related genes or pluripotent stem cells having isoforms associated with Alzheimer's disease.

A description will be given below of each step of the production method of the present embodiment. First, in step (a), pluripotent stem cells are formed into an embryoid body in the presence of a SMAD inhibitor. Step (a) is preferably performed for approximately 7 days. This step makes it possible to induce pluripotent stem cells to differentiate into nervous system cells. As SMAD inhibitors, it is preferable to use a combination of a BMP inhibitor and a TGF-β inhibitor.

As BMP inhibitors, it is possible to use Dorsomorphin (CAS No.: 866405-64-3), DMH1 (CAS No.: 1206711-16-1), LDN-193189 (CAS No.: 1062368-24-4), and the like. One of the above may be used alone or a combination of two or more may be used. Examples of the amount of the BMP inhibitor added to the medium include approximately 1 to 3 μM.

In addition, as TGF-β inhibitors, it is possible to use A83-01 (CAS No.: 909910-43-6), SB-431542 (CAS No.: 301836-41-9), RepSox (CAS No.: 446859-33-2), and the like. One of the above may be used alone or a combination of two or more may be used. Examples of the amount of the TGF-β inhibitor added to the medium include approximately 1 to 3 μM.

It is possible to use any serum-free cell culture basal medium as the basal medium. Examples thereof include a defined synthetic medium buffered at pH 7.2 or higher and pH 7.6 or lower using a carbonate-based buffer solution or the like. More specifically, examples thereof include Advanced-Dulbecco's modified Eagle's medium/Ham's F-12 mixed medium (DMEM/F12), Neurobasal medium (Thermo Fisher Scientific Inc.), Neurobasal Plus medium (Thermo Fisher Scientific Inc.), RPMI1640 medium, advanced RPM1 medium, and the like. A SMAD inhibitor and other additives are added to the basal medium and the pluripotent stem cells are cultured.

In the production method of the present embodiment, it is preferable to perform all the steps feeder-free without using feeder cells. That is, the pluripotent stem cells are preferably cultured feeder-free and steps (a) to (c) are also preferably performed feeder-free. Due to this, the culturing operation is simplified and it is possible to prevent feeder cells from being mixed into the brain organoid.

A SMAD inhibitor and a GSK3β inhibitor may be added to the medium for the final 1 to 2 days of step (a). The SMAD inhibitor and GSK3β inhibitor are the same as in step (b) described below.

A step for culturing the pluripotent stem cells in the presence of less than 100 ng/mL of fibroblast growth factor-2 (FGF2) may be further performed before step (a). The amount of FGF2 added to the medium is preferably less than 100 ng/mL and may be, for example, 50 ng/mL or may be, for example, 10 ng/mL.

The FGF2 may be human-derived or mouse-derived, but is preferably human-derived.

In a case where pluripotent stem cells are cultured feeder-free, it is normal to add 100 ng/mL of FGF2 to the medium. In this regard, the inventors clarified that the production efficiency of brain organoids having an aggregated tau protein was increased by decreasing the amount of FGF2 added to the medium.

When the amount of FGF2 added is excessively small, the pluripotent stem cells may undergo differentiation. In addition, when the amount of FGF2 added is excessively large, it tends to be difficult to obtain a neuroepithelium-like structure.

In addition, for example, in a case where the amount of FGF2 added to the medium is 10 ng/mL, it becomes difficult to maintain the pluripotent stem cells when the culturing is continued for approximately 3 weeks or longer. For this reason, in a case where the pluripotent stem cells are cultured feeder-free in the presence of 10 ng/mL FGF2, the culturing time is preferably 4 weeks or shorter.

Subsequently, in step (b), the embryoid body after step (a) are embedded in an extracellular matrix and three-dimensionally cultured in the presence of a SMAD inhibitor and a GSK3β inhibitor to form an organoid. Here, the embryoid body are preferably embedded in the extracellular matrix without being dispersed. In a case where the embryoid body are dispersed, the method for dispersing the embryoid body is not particularly limited and examples thereof include physical methods, enzymatic treatment methods, and the like, but an enzymatic treatment method is preferable from the viewpoint of not damaging the cells. As enzymes used in the enzymatic treatment method, it is possible to use TrypLE Express (Thermo Fisher Scientific Inc.), TrypLE Select (Thermo Fisher Scientific Inc.), trypsin, collagenase, dispase I, and the like. Step (b) is preferably performed for approximately 7 days.

Examples of extracellular matrices include type IV collagen, laminin, heparan sulfate proteoglycan, entactin, and the like. As the extracellular matrix, for example, a commercially available extracellular matrix such as Matrigel (registered trademark, manufactured by Corning Incorporated) may be used.

As the SMAD inhibitor, it is preferable to use the TGF-β inhibitor described above. Two or more SMAD inhibitors are preferably used in combination in step (a), but one may be used alone in step (b). Among the above, it is preferable to use SB-431542 as the SMAD inhibitor in step (b). Examples of the amount of the SMAD inhibitor added to the medium include approximately 1 to 5 μM.

Examples of GSK3β inhibitors include CHIR99021 (CAS No.: 252917-06-9), Kenpaullone (CAS No.: 142273-20-9), 6-Bromoindirubin-3'-oxime (CAS No.: 029-16241), and the like. Examples of the amount of the GSK3β inhibitor added to the medium include approximately 1 to 5 μM. Among the above, it is preferable to use CHIR99021.

Subsequently, in step (c), the organoids after step (b) are extracted from the extracellular matrix and suspension-cultured in a medium. The suspension-culturing is preferably performed using a bioreactor. It is possible to use a commercially available bioreactor.

In at least a part of step (c), it is preferable to add leukemia inhibitory factor (LIF) to the medium. Examples of the amount of LIF added include approximately 5 to 50 ng/mL. The addition of LIF to the medium may be performed during only a part of step (c) or during all of step (c). The LIF may be human-derived or mouse-derived, but is preferably human-derived. The inventors clarified that performing suspension-culturing in the presence of LIF increases the production efficiency of brain organoids having an aggregated tau protein.

It is preferable to perform step (c) of 3 weeks or longer. As described below in the Examples, it was clarified that, by performing step (c) of 3 weeks or longer (5 weeks or longer from the start of step (a)), preferably 6 weeks or longer (8 weeks or longer from the start of step (a)), and more preferably for 11 weeks or longer (13 weeks or longer from the start of step (a)), the aggregated tau protein in the brain organoids was significantly increased.

The medium in step (c) may include additives in addition to LIF. Examples of additives include N2 supplement (Thermo Fisher Scientific Inc.), B27 supplement (Thermo Fisher Scientific Inc.) and the like. The medium including LIF, N2 supplement, and B27 supplement may be referred to below as a "differentiation induction medium".

In addition, in the latter half of step (c), the medium may be made to further contain additives. Examples of additives include Brian-derived neurotrophic factor (BDNF), glial derived neurotrophic factor (GDNF), cAMP, and the like in addition to the LIF, N2 supplement, and B27 supplement described above. The medium including LIF, N2 supplement, B27 supplement, BDNF, GDNF, and cAMP may be referred to below as a "neural maturation medium".

It is preferable to perform at least a part of step (c) in the presence of more than 20% by volume of oxygen. More than 20% by volume of oxygen is an oxygen concentration higher than the oxygen concentration in normal air (which is approximately 20% by volume). The concentration of oxygen in step (c) is preferably more than 20% by volume and may be, for example, 30% by volume, 40% by volume, or 50% by volume. The inventors clarified that performing suspension-culturing under a higher oxygen concentration than normal increases the production efficiency of brain organoids having an aggregated tau protein.

The period during which the oxygen concentration is increased may be, for example, a period from approximately 7 days after the start of step (c) to the end of the culturing (the end of step (e) described below), a period from approximately 14 days after the start of step (c) to the end of the culturing, or a period from approximately 21 days after the start of step (c) to the end of the culturing.

Subsequently, in step (d), the brain organoid after step (c) is forced to express the mutant microtubule associated protein tau (MAPT) gene.

It is possible to use 4R0N, 4R1N, and 4R2N isoforms as the tau protein. Examples of mutant MAPT genes include genes encoding tau protein having a P301L mutation (amino acid sequence shown in SEQ ID NO: 1), tau protein having a P301S mutation (amino acid sequence shown in SEQ ID NO: 2), and the like.

Forced expression of the mutant MAPT gene is preferably performed by gene introduction using a virus and particularly preferably by gene introduction using an adeno-associated virus (AAV). It is possible to perform the gene introduction by creating an AAV vector in which a mutant tau protein gene linked to a CAG promoter, an SYN1 promoter, an EF1α promoter, a CMV promoter, or the like is inserted. As an AAV, it is possible to use AAV1, AAV2, AAV4, AAV5, AAV7, AAV8, AAV9, AAVrh10, AAV-DJ, AAV-DJ/8, AAV-PHP.B, AAV-PHP.eB, and the like.

In addition, the gene introduction using AAV is preferably performed by inserting a glass tube into the brain organoid and injecting the AAV. As described below in the Examples, it was clarified that the injection of virus particles (a virus particle suspension) into brain organoids significantly increases aggregated tau protein compared to the addition of virus particles into the medium of the brain organoids.

For the injection of the virus particles, for example, it is possible to use an electric microinjector. The injection rate of the virus particle suspension into the brain organoids is preferably, for example, 50 to 200 nL/min, and is able to be, for example, approximately 100 nL/min.

Subsequently, in step (e), the brain organoids after step (d) are further suspension-cultured to obtain brain organoids having an aggregated tau protein. The suspension-culturing is preferably performed in the presence of more than 20% by volume of oxygen.

Step (e) is preferably performed for 5 weeks or longer. As described below in the Examples, when step (e) is performed for 5 weeks or longer, the aggregated tau protein in the brain organoids tends to increase significantly.

[Brain Organoids Having Aggregated Tau Protein]

In one embodiment, the present invention provides a brain organoid having an aggregated tau protein, in which, in a cross-section, an average ratio of an area of a region where a phosphorylated tau protein is present is 2% or more with respect to the total area of the cross-section, or, in a cross-section, an average ratio of an area of a region where an aggregated tau protein is present is 1% or more with respect to the total area of the cross-section. As long as the brain organoid of the present embodiment includes a cross-section that satisfies the area ratio described above, it is not necessary for all the cross-sections to satisfy the area ratio described above.

The brain organoid of the present embodiment is preferably derived from humans. In related art, there are no reports of a technique for efficiently producing an aggregated tau protein. On the other hand, since it is possible for the brain organoids of the present embodiment to be efficiently produced, use as a tau aggregation model is possible. For example, the present invention is useful as a model for researching the pathogenesis of tauopathy and as a model for studying preventive methods and therapeutic methods. It is possible to produce the brain organoid of the present embodiment by the production method described above.

The brain organoid of one embodiment has an aggregated tau protein and, in a cross-section, the average ratio of the area of the region where a phosphorylated tau protein is present with respect to the total area of the cross-section is 2% or more, preferably 3% or more, and more preferably 5% or more. As long as the brain organoid of the present embodiment includes a cross-section that satisfies the area ratio described above, it is not necessary for all the cross-sections to satisfy the area ratio described above.

It is possible to detect the region where the phosphorylated tau protein is present, for example, by immunostaining using an antibody against the phosphorylated tau protein. As an antibody against the phosphorylated tau protein, for example, it is possible to use an anti-phosphorylated tau antibody (clone AT8, Fujirebio Inc.), a PHF-1 anti-phospho tau antibody (courtesy of P. Davies), or the like. It is possible to use other antibodies as long as the antibodies are able to detect the phosphorylated tau protein.

The brain organoid of one embodiment has an aggregated tau protein, and, in a cross-section, the average ratio of the area of the region where an aggregated tau protein is present with respect to the total area of the cross-section is 1% or more, preferably 2% or more, and more preferably 5% or more. As long as the brain organoid of the present embodiment includes a cross-section that satisfies the area ratio described above, it is not necessary for all the cross-sections to satisfy the area ratio described above.

It is possible to detect the region where the aggregated tau protein (misfolded tau protein or tau protein in which structural changes occurred) is present, for example, by immunostaining using an antibody against the aggregated tau protein. As an antibody against the aggregated tau protein, for example, it is possible to use a monoclonal antibody (clone MC1), a monoclonal antibody (clone Alz50), and the like. Aggregated tau proteins are considered to be phosphorylated.

As described below, it is possible to use the brain organoids of the present embodiment for screening prophylactic or therapeutic agents for tauopathy. Accordingly, in one embodiment, the present invention provides a screening kit for a prophylactic or therapeutic agent for tauopathy, the kit including a brain organoid having an aggregated tau protein. The brain organoid having an aggregated tau protein is the same as described above.

[Method for Screening for Therapeutic Agent for Tauopathy]

In one embodiment, the present invention provides a method for screening for a therapeutic agent for tauopathy, the method including a step for culturing the brain organoid having an aggregated tau protein as described above in the presence of a test substance, and a step for measuring an amount of a phosphorylated tau protein present or an amount of an aggregated tau protein present in the brain organoid, in which a decrease in the amount of the phosphorylated tau protein present or the amount of the aggregated tau protein present, compared to in the absence of the test substance, indicates that the test substance is a therapeutic agent for tauopathy.

The test substance is not particularly limited and examples thereof include natural compound libraries, synthetic compound libraries, existing drug libraries, metabolite libraries, and the like.

It is possible to measure the amount of phosphorylated tau protein present, for example, by subjecting brain organoids to immunostaining, Western blotting, ELISA, or the like, using phosphorylated tau antibodies.

It is possible to measure the amount of aggregated tau protein present, for example, by subjecting brain organoids to immunostaining using an antibody against the aggregated tau protein, Western blotting, ELISA, or the like.

For example, in a case where the amount of the phosphorylated tau protein present or the amount of the aggregated tau protein present in brain organoids cultured in the presence of the test substance is decreased compared to a control, it is possible to say that the test substance is a therapeutic agent for tauopathy. Here, examples of the control include brain organoids cultured in the absence of a test substance and the like.

It is possible to screen therapeutic agents for tauopathy using the screening method of the present embodiment. It is possible to say that the therapeutic agent for tauopathy obtained by the screening method of the present embodiment is a drug that decreases or eliminates the amount of the aggregated tau protein present when administered after the formation of the aggregated tau protein.

[Method for Screening for Prophylactic or Therapeutic Agent for Tauopathy]

In one embodiment, the present invention provides a method for screening a prophylactic or a therapeutic agent for tauopathy, the method including a step (a) of culturing pluripotent stem cells in the presence of a SMAD inhibitor to form an embryoid body, a step (b) of embedding the embryoid body in an extracellular matrix and three-dimensionally culturing the embryoid body in the presence of a SMAD inhibitor and a GSK3β inhibitor to form an organoid that includes neural precursor cells, a step (c) of extracting the organoid from the extracellular matrix and suspension-culturing the organoid in the presence of LIF to form a brain organoid, a step (d) of forcing the brain organoid to express a mutant MAPT gene, a step (e) of further suspension-culturing the brain organoid for 5 weeks or longer after step (d), and a step (f) of measuring an amount of a phosphorylated tau protein present or an amount of an aggregated tau protein present in the brain organoid during step (e) or after step (e), in which at least a part of steps (c) to (e) is performed in the presence of a test substance and a decrease in the amount of the phosphorylated tau protein present or the amount of the aggregated tau protein present, as measured in step (f), compared to in the absence of the test substance, indicates that the test substance is a prophylactic or therapeutic agent for tauopathy.

In the screening method of the present embodiment, steps (a) to (e) are the same as steps (a) to (e) in the method for producing a brain organoid having an aggregated tau protein as described above, but at least a part of step (c) to (e) is performed in the presence of a test substance, which is a point different from the production method described above.

The test substances are the same as described above for the method for screening for a therapeutic agent for tauopathy.

In the screening method of the present embodiment, the amount of phosphorylated tau protein present or the amount of aggregated tau protein present in brain organoids is measured in step (f). It is possible to measure the amount of phosphorylated tau protein present and the amount of aggregated tau protein present by the same methods described above.

In step (f), in a case where the amount of the phosphorylated tau protein or the amount of the aggregated tau protein present in brain organoids cultured in the presence of the test substance is decreased compared to the control, it is possible to say that the test substance is a prophylactic or therapeutic agent for tauopathy. Here, examples of the control include brain organoids cultured in the absence of a test substance and the like.

It is possible to say that the prophylactic agent for tauopathy obtained by the screening method of the present embodiment is a drug that suppresses or prevents the formation of aggregated tau protein present when administered before the formation of the aggregated tau protein. In addition, it is possible to say that the therapeutic agent for tauopathy obtained by the screening method of the present embodiment is a drug that decreases or eliminates the amount of aggregated tau protein present when administered after the formation of the aggregated tau protein.

EXAMPLES

A more detailed description will be given of the present invention with reference to Examples, but the present invention is not limited to the following Examples.

Experimental Example 1

(Production of Brain Organoid Having Aggregated Tau Protein 1)

First, pluripotent stem cells were cultured and a brain organoid was produced. As pluripotent stem cells, 201B7, which is a wild-type human iPS cell line, and PS1-2 and PS2-2, which are human iPS cell lines derived from Alzheimer's disease patients, were used.

It was clarified that PS1-2 cells have a genetic mutation in the PS1 gene that causes an amino acid mutation (A246E) from alanine to glutamic acid at the 246th amino acid of the PS1 protein. In addition, it was clarified that PS2-2 cells have a genetic mutation in the PS2 gene that causes an amino acid mutation (N141I) from asparagine to isoleucine at the 141st amino acid of the PS2 protein.

FIG. 1 is a diagram showing a schedule for producing brain organoids. The culturing of each pluripotent stem cell was performed feeder-free without using feeder cells. First, each cell was cultured in a medium including 10 ng/mL FGF2 for 1 to 3 weeks.

Subsequently, on day 0 of culturing (Day 0), each of the cells dissociated into single cells was suspended in an iPS medium including 2 μM Dorsomorphin (SIGMA Corp.), 2 μM A83-01 (Tocris Bioscience), and 10 μM Y27632 (Nacalai Tesque Inc.) and including no FGF2 and seeded in a 96-well plate. On the first day of culturing (Day 1), a medium obtained by extracting Y27632 from the medium described above was added in the same amount. On the third day of culturing (Day 3), half of the medium was replaced. In FIG. 1, "Dorso" indicates Dorsomorphin and "A83" indicates A83-01. As a result, embryoid bodies were formed.

Subsequently, on the fifth to sixth days of culturing (Day 5 to 6), half of the medium was replaced with a nerve induction medium. The composition of the nerve induction medium was DMEM/F12, GlutaMAX (Thermo Fisher Scientific Inc.), 1 μM CHIR99021 (Cellagen Technology), 1 μM SB-431542 (Cellagen Technology), 1×N2 supplement (Thermo Fisher Scientific Inc.), 1×NEAA (Thermo Fisher Scientific Inc.), and 1× penicillin-streptomycin. In FIG. 1, "CHIR" indicates CHIR99021 and "SB" indicates SB-431542.

Subsequently, on the seventh day of culturing (Day 7), each cell was embedded in Matrigel (BD Biosciences) and cultured in a nerve induction medium for an additional 6 days. Half of the medium was replaced every other day.

Subsequently, on the 14th day of culturing (Day 14), organoids formed by mechanical dissociation of the Matrigel were extracted by pipetting using a 5 mL pipette. Subsequently, the organoids were suspended in a differentiation induction medium and placed in a bioreactor (Able Corp.) for suspension-culturing. The composition of the differentiation induction medium was DMEM/F12, GlutaMAX (Thermo Fisher Scientific Inc.), 1×N2 supplement (Thermo Fisher Scientific Inc.), 1×B27 supplement (Thermo Fisher Scientific Inc.), 2.5 μg/mL insulin (SIGMA Corp.), 0.1 nM 2-mercaptoethanol, 1×NEAA (Thermo Fisher Scientific Inc.), 1× penicillin/streptomycin, and 10 ng/mL LIF (Merck Millipore). The medium was replaced every 2 to 3 days. In FIG. 1, "N2" indicates N2 supplement, "B27" indicates B27 supplement, and "LIF" indicates LIF.

From the 28th day of culturing (Day 28), the oxygen concentration in the incubator was set to 40% by volume.

From the 71st day of culturing (Day 71), the differentiation induction medium was replaced with a neural maturation medium and the suspension-culturing was continued. The composition of the neural maturation medium was Neurobasal Plus (Thermo Fisher Scientific Inc.), 1×B27 supplement (Thermo Fisher Scientific Inc.), 20 ng/mL BDNF (Peprotech), 20 ng/mL GDNF (Peprotech), 0.5 mM cAMP (SIGMA Corp.), 1×GlutaMAX (Thermo Fisher Scientific Inc.), 0.2 mM ascorbic acid (SIGMA Corp.), 1× Antibiotic-Antimycotic (Thermo Fisher Scientific Inc.), and 10 ng/mL LIF (Merck Millipore). The medium was replaced every 2 to 3 days. In FIG. 1, "B27" indicates B27 supplement, "BDNF" indicates BDNF, "GDNF" indicates GDNF, and "cAMP" indicates cAMP. As a result, brain organoids were formed.

A mutant MAPT gene was introduced into each brain organoid on the 84th day of culturing (Day 84, 12 weeks). A gene encoding a tau protein (the amino acid sequence is shown in SEQ ID NO: 1) having a P301L mutation was used as the mutant MAPT gene. In more detail, an AAV virus expression plasmid incorporating a mutant MAPT gene downstream of the CAG promoter was introduced into packaging cells to prepare AAV virus particles (may be referred to below as "AAV(PHP.B)-CAG-Tau(1N4R)-P301L").

In addition, for comparison, AAV virus particles expressing green fluorescent protein (EGFP) instead of the mutant MAPT gene (may be referred to below as "AAV(PHP.B)-CAG-EGFP") were also prepared.

The titer of the virus particles (AAV(PHP.B)-CAG-Tau (1N4R)-P301L) was $1.32\times10^{13}$ VG/mL (here, "VG" means "Vector Genome"). In addition, the titer of the virus particles (AAV(PHP.B)-CAG-EGFP) was $2\times10^{13}$ VG/mL.

Each virus particle was introduced by adding 0.5, 2, or 10 μL at a time into the medium of the brain organoid or by inserting a glass tube into the brain organoid and injecting the virus suspension. The injection was performed using an electric microinjector (product name "BJ-110", BEX Co., Ltd.) with 2 μL of virus particles per brain organoid at an introduction rate of 100 nL/min.

After that, the suspension-culturing of the brain organoids was continued and, on the 120th day of culturing (Day 120, 106th day after the start of suspension-culturing), each brain organoid was extracted and fixed with 4% paraformaldehyde. Subsequently, the fixed organoid was embedded in an embedding agent (product name "O.C.T. compound", product no. 45833, Sakura Finetek Japan Co., Ltd.) to prepare sections.

Subsequently, each section was immunostained using an anti-tau antibody (clone RTM38, Fujifilm Wako Pure Chemical Industries, Ltd.), an anti-phosphorylated tau antibody (clone ATB, Fujirebio Inc.), and an antibody against the aggregated tau protein (clone MC1) and the tau protein aggregation was examined. In addition, the nucleus was stained with Hoechst 33342.

Figure 2:
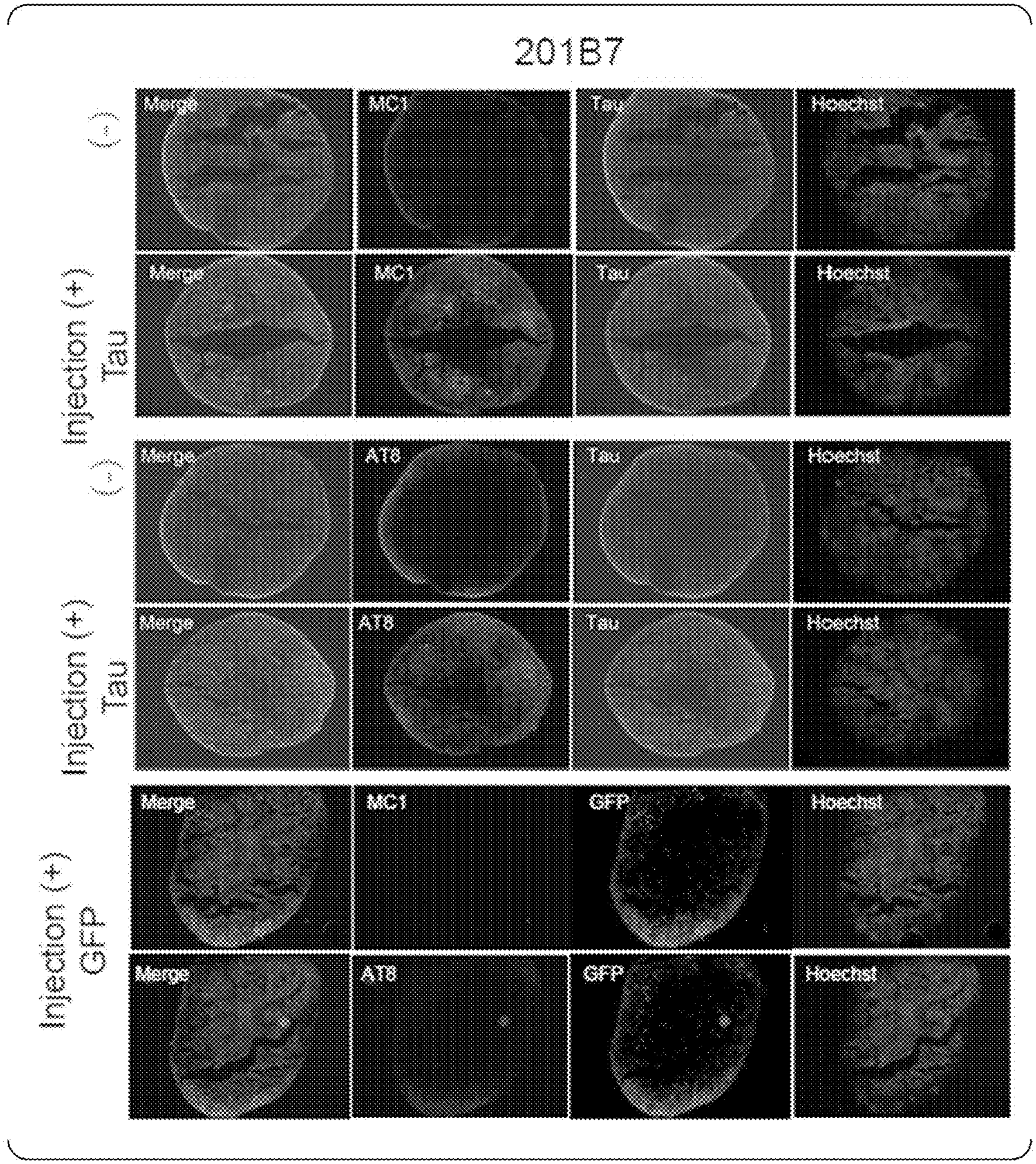
FIG. 2 is a fluorescence microscope photograph showing the results of immunohistochemical staining in Experimental Example 1.
Figure 3:
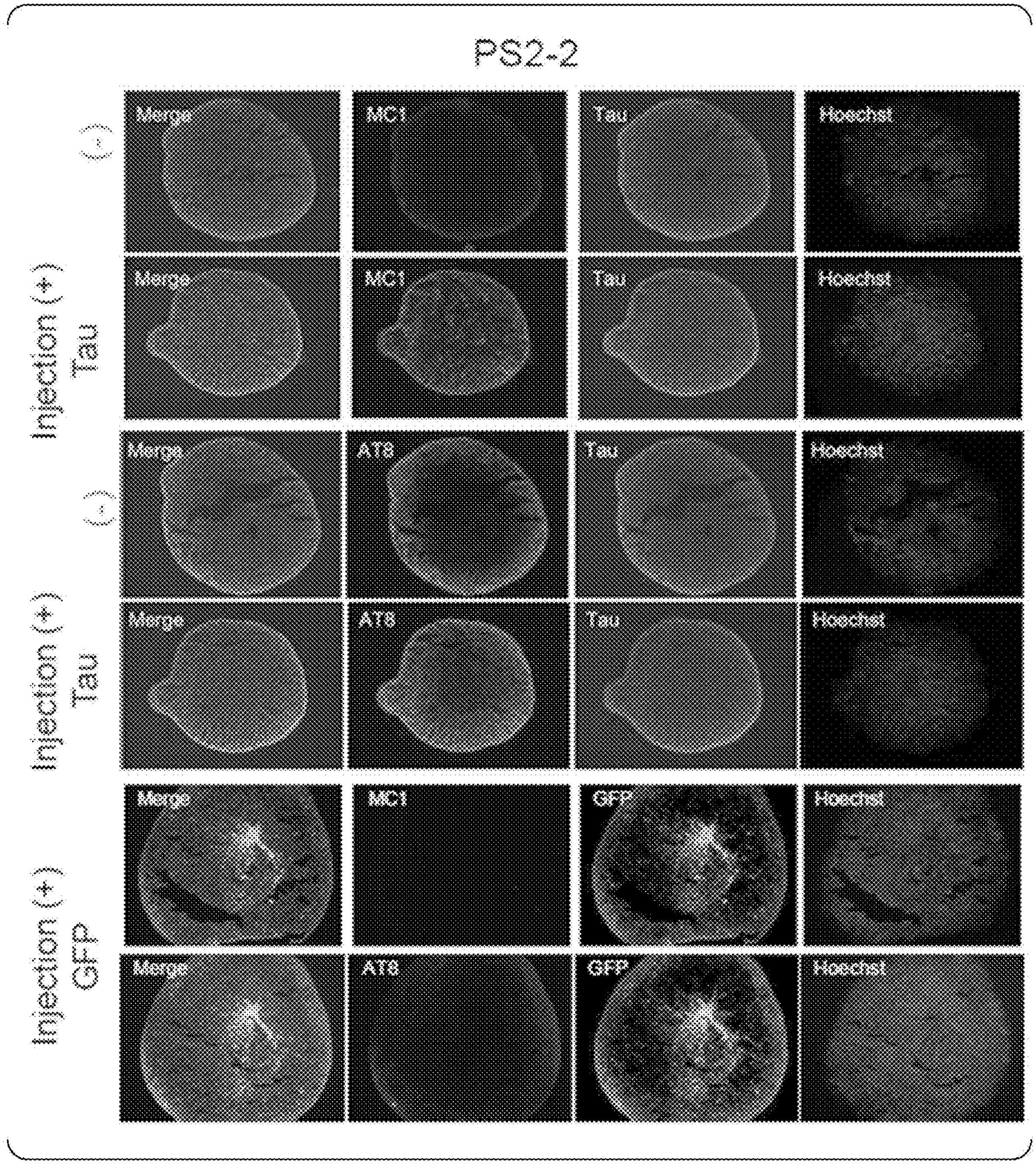
FIG. 3 is a fluorescence microscope photograph showing the results of immunohistochemical staining in Experimental Example 1.
Figure 4:
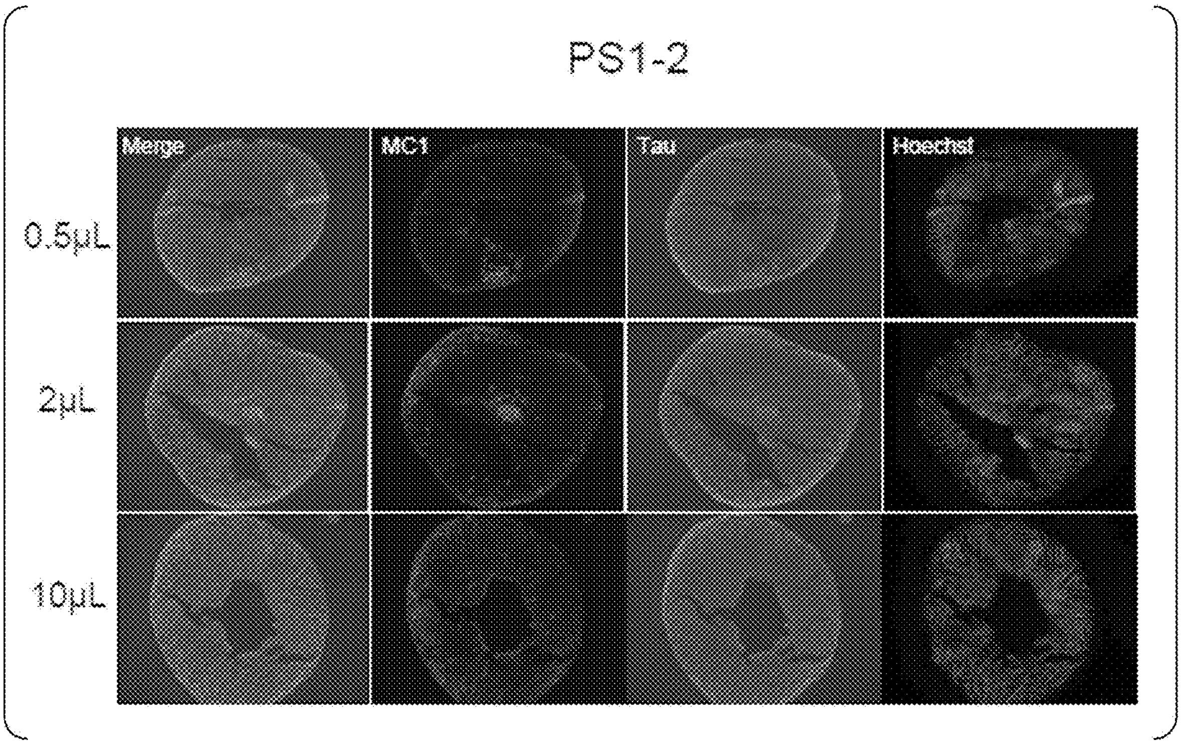
FIG. 4 is a fluorescence microscope photograph showing the results of immunohistochemical staining in Experimental Example 1.

FIG. 2 to FIG. 4 are fluorescence microscope photographs showing the results of immunohistochemical staining FIG. 2 shows the results of brain organoids produced from 201B7 cells and FIG. 3 shows the results of brain organoids produced from PS2-2 cells.

In FIG. 2 and FIG. 3, "Injection (+) Tau" indicates the results for introducing AAV(PHP.B)-CAG-Tau(1N4R)-P301L by injection and (−) indicates that virus particles are not introduced. In addition, "Injection (+) GFP" indicates the results for introducing AAV(PHP.B)-CAG-EGFP by injection. In addition, "MC1" indicates the results for staining with an MC1 antibody, "AT8" indicates the results for staining with an anti-phosphorylated tau antibody, "Tau" indicates the results for staining with an anti-tau antibody, "GFP" indicates the results for detecting EGFP fluorescence, "Hoechst" indicates the results for staining the nucleus with Hoechst 33342, and "Merge" indicates the results for merging photographs.

As a result, it was clear that the phosphorylated tau protein and the aggregated tau protein were significantly increased in brain organoids into which AAV(PHP.B)-CAG-Tau(1N4R)-P301L was introduced by injection.

FIG. 4 is a fluorescence microscope photograph showing the results for adding 0.5, 2, and 10 μL of AAV(PHP.B)-CAG-Tau(1N4R)-P301L to a medium of a brain organoid produced from PS1-2 cells.

In FIG. 4, "MC1" indicates the results for staining with an MC1 antibody, "Tau" indicates the results for staining with an anti-tau antibody, "Hoechst" indicates the results for staining the nucleus with Hoechst 33342, and "Merge" indicates the results for merging photographs. In addition, "0.5 μL", "2 μL", and "10 μL" indicate the results for adding each of 0.5, 2, and 10 μL of AAV(PHP.B)-CAG-Tau(1N4R)-P301L.

As a result, it was clear that the aggregated tau protein was increased significantly by injecting virus particles into brain organoids compared to adding virus particles to the brain organoid medium.

Figure 5A:
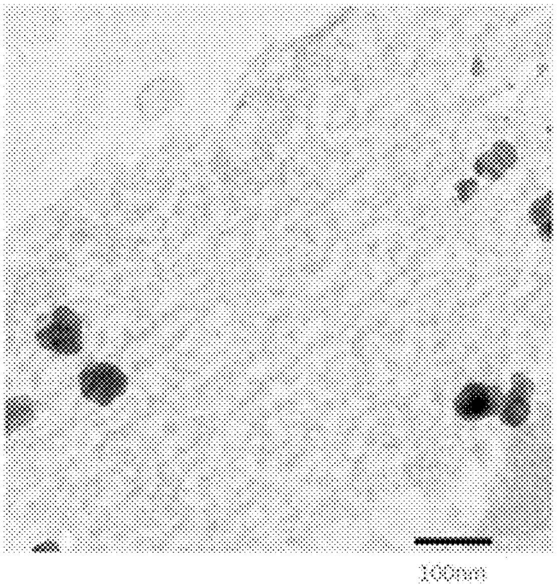
FIG. 5A is a photograph showing the results of observing brain organoids produced from PS2-2 cells by electron microscopy in Experimental Example 1.
Figure 5B:
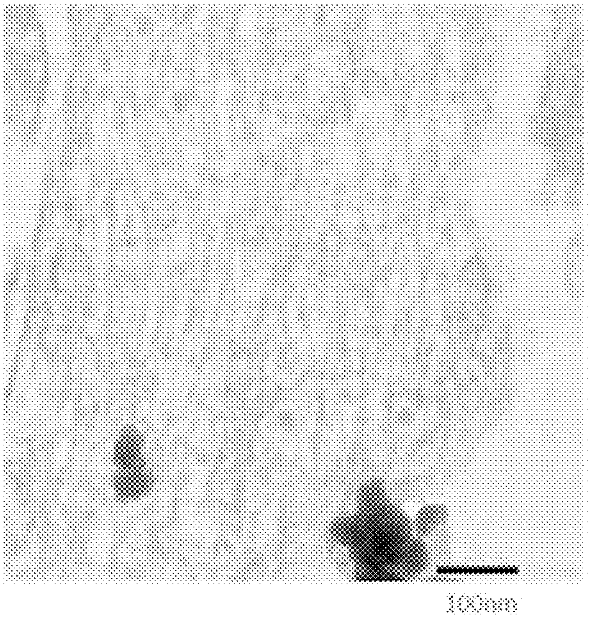
FIG. 5B is a photograph showing the results of observing brain organoids produced from PS2-2 cells by electron microscopy in Experimental Example 1.

FIG. 5A and FIG. 5B are photographs showing the results after AAV(PHP.B)-CAG-Tau(1N4R)-P301L was injected into brain organoids produced from PS2-2 cells and the brain organoids were fixed after 5 weeks and observed by immunoelectron microscopic analysis using an MC1 antibody. The scale bar is 100 nm. As a result, tau fiber-like structures were observed. This result indicates that it is possible to use the brain organoids of the present experimental example as a tau aggregation model.

Experimental Example 2

(Production of Brain Organoids Having Aggregated Tau Protein 2)

Brain organoids were produced by culturing pluripotent stem cells in the same manner as in Experimental Example 1. A wild-type human iPS cell line 201B7 was used as the pluripotent stem cells.

A mutant MAPT gene was introduced into each brain organoid on days 35 to 41 of culturing (5 weeks), days 56 to 62 of culturing (8 weeks), and days 91 to 97 of culturing (13 weeks). Introduction of the mutant MAPT gene was carried out by injecting the virus particles (AAV(PHP.B)-CAG-Tau (1N4R)-P301L) described above using a gas injector. In addition, for comparison, a group injected with AAV virus particles expressing EGFP (AAV(PHP.B)-CAG-EGFP) instead of the mutant MAPT gene was also prepared.

After that, the suspension-culturing of each brain organoid was continued and each brain organoid was extracted and fixed with 4% paraformaldehyde 5 weeks after the introduction of the virus particles. Subsequently, the fixed organoids were then embedded in resin and sections were prepared.

Subsequently, each section was immunostained using an anti-tau antibody (clone RTM38, Fujifilm Wako Pure Chemical Industries, Ltd.), an anti-phosphorylated tau antibody (clone AT8, Fujirebio Inc.), and an antibody against the aggregated tau protein (clone MC1) and the tau protein aggregation was examined. In addition, the nucleus was stained with Hoechst 33342.

Figure 6:
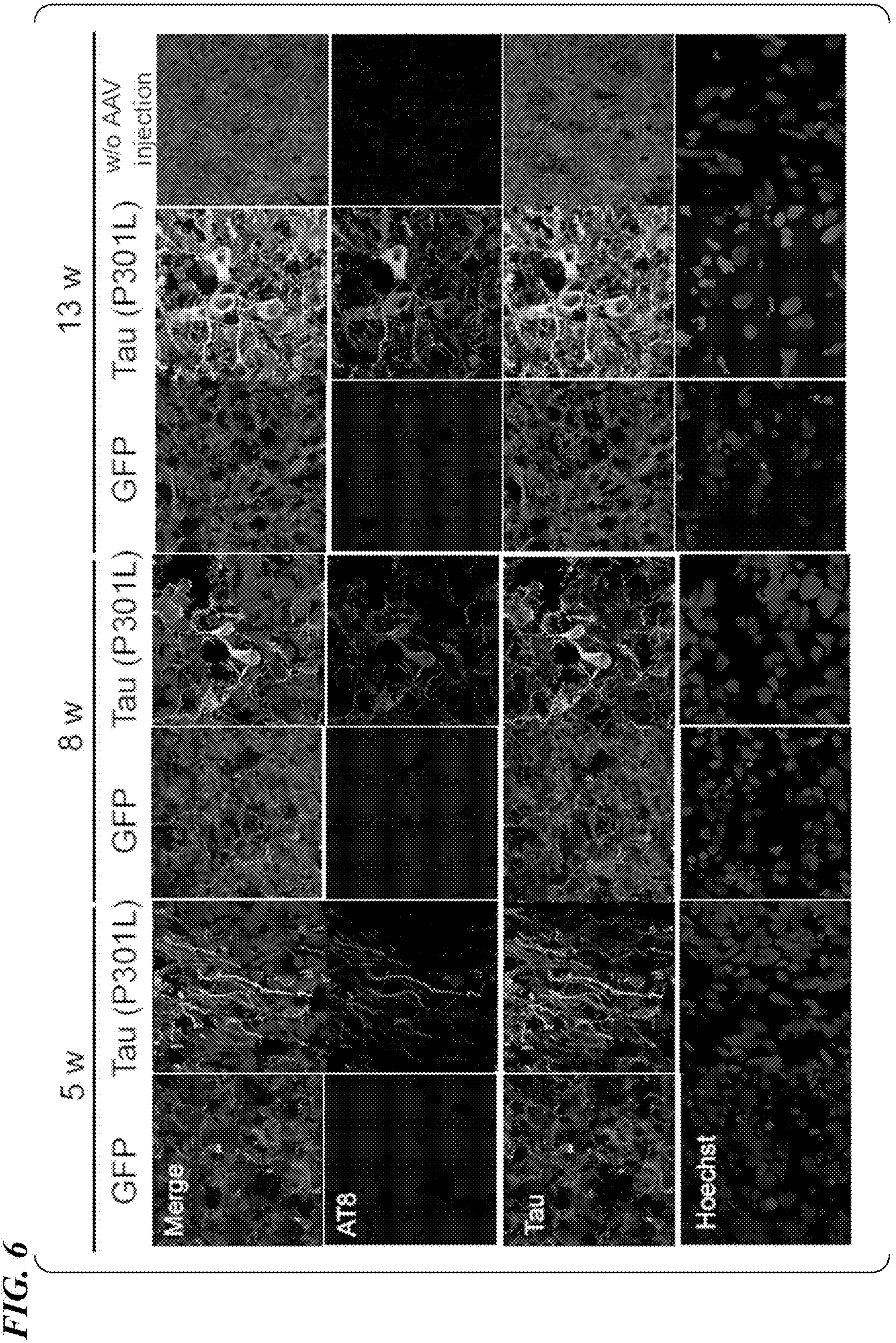
FIG. 6 is a fluorescence microscope photograph showing the results of immunohistochemical staining in Experimental Example 2.
Figure 7:
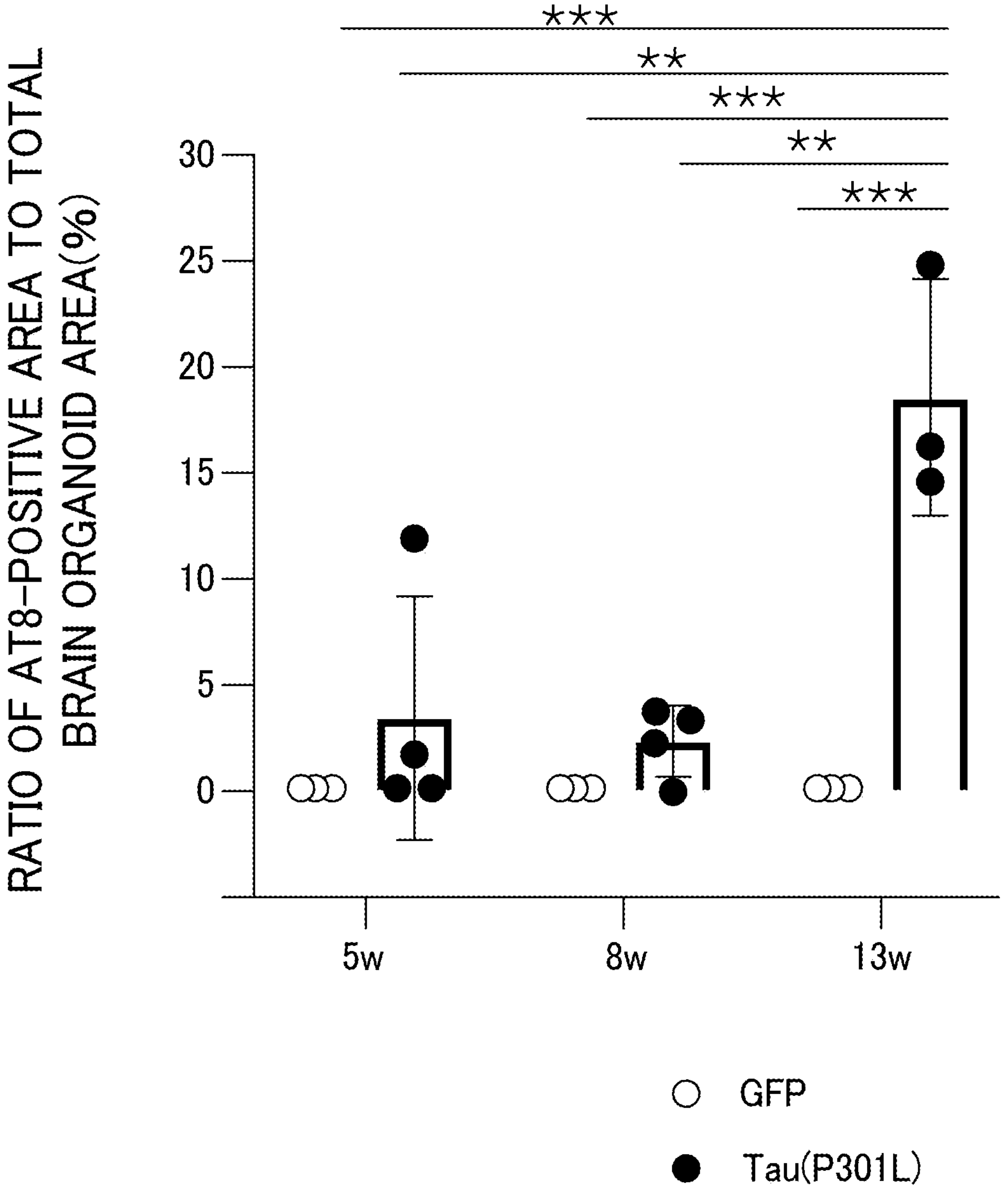
FIG. 7 is a graph showing the quantified results of the results of FIG. 6.

FIG. 6 is a fluorescence microscope photograph showing the results of immunohistochemical staining. In addition, FIG. 7 is a graph showing the quantified results of the results of FIG. 6. In FIG. 6 and FIG. 7, "5w", "8w", and "13w" indicate the results for injecting virus particles into each brain organoid on each of days 35 to 41 of culturing (5 weeks), days 56 to 62 of culturing (8 weeks), and days 91 to 97 of culturing (13 weeks). In addition, "GFP" indicates the results for introducing AAV(PHP.B)-CAG-EGFP and "Tau (P301L)" indicates the results for introducing AAV(PHP.B)-CAG-Tau(1N4R)-P301L.

In addition, in FIG. 6, "AT8" indicates the results for staining with an anti-phosphorylated tau antibody, "Tau" indicates the results for staining with an anti-tau antibody, "Hoechst" indicates the results for staining the nucleus with Hoechst 33342, and "Merge" indicates the results for merging photographs. In addition, "w/o AAV injection" indicates the results for not injecting AAV virus particles.

In addition, in FIG. 7, the vertical axis indicates the ratio (%) of the area of a region where a phosphorylated tau protein is present (the region stained with an AT8 antibody) with respect to the total area of the brain organoid cross-section. In addition, the numerical values indicate the average value±standard deviation, "" indicates that there was a significant difference at $P<0.004$ and "*" indicates that there was a significant difference at $P<0.001$.

As a result, it was clear that, in all of the brain organoids from days 35 to 41 of culturing (5 weeks), days 56 to 62 of culturing (8 weeks), and days 91 to 97 of culturing (13 weeks), when AAV(PHP.B)-CAG-Tau(1N4R)-P301L was introduced by injection, the average ratio of the area of a region where a phosphorylated tau protein was present (the region stained with an AT8 antibody) with respect to the total area of the brain organoid cross-section was 2% or more.

In particular, it was clear that, when AAV(PHP.B)-CAG-Tau(1N4R)-P301L was introduced by injection into brain organoids on days 91 to 97 of culturing (13 weeks), the ratio of the area of the region where a phosphorylated tau protein as present (the region stained with an AT8 antibody) with respect to the total area of the brain organoid cross-section increased significantly.

Figure 8:
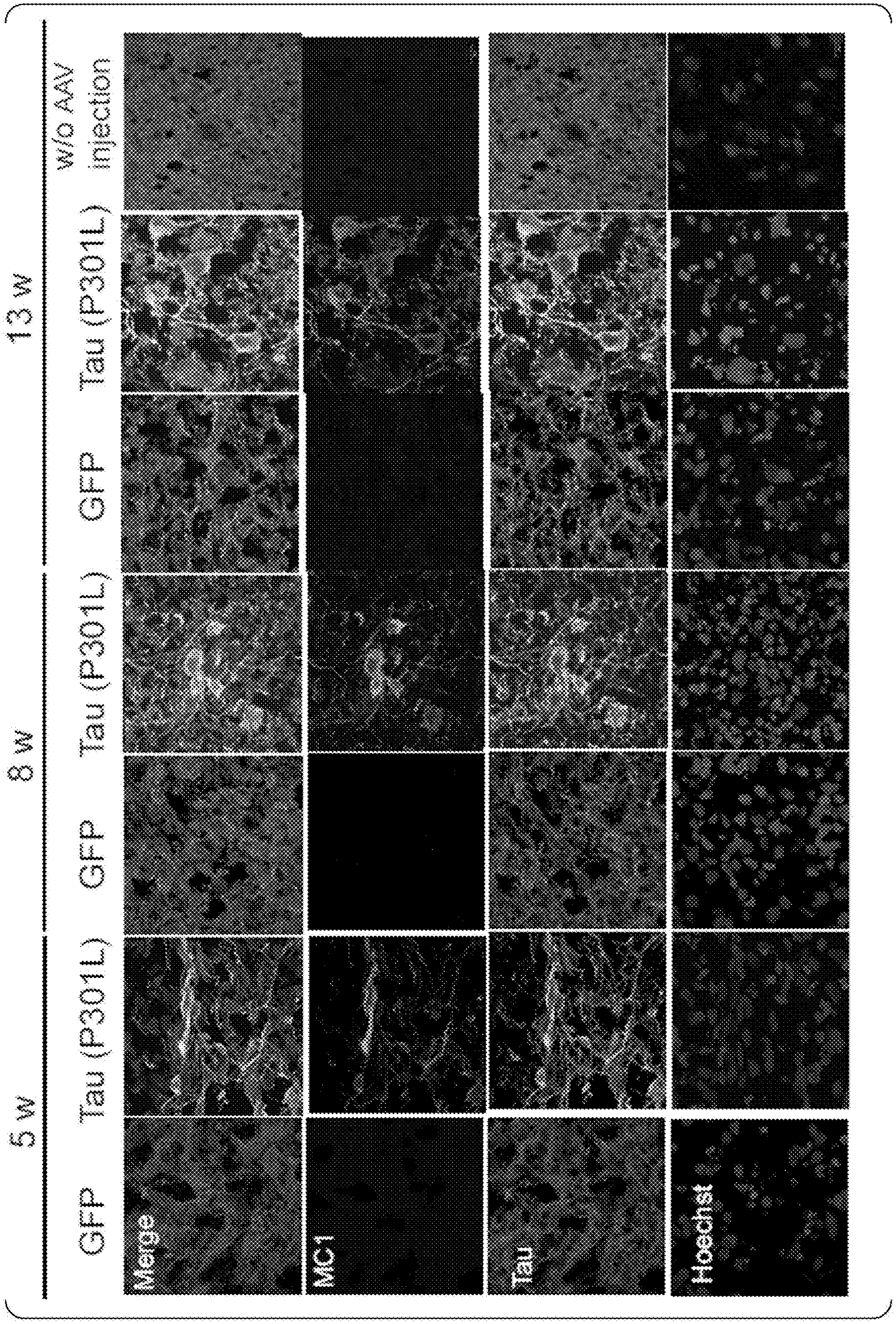
FIG. 8 is a fluorescence microscope photograph showing the results of immunohistochemical staining in Experimental Example 2.
Figure 9:
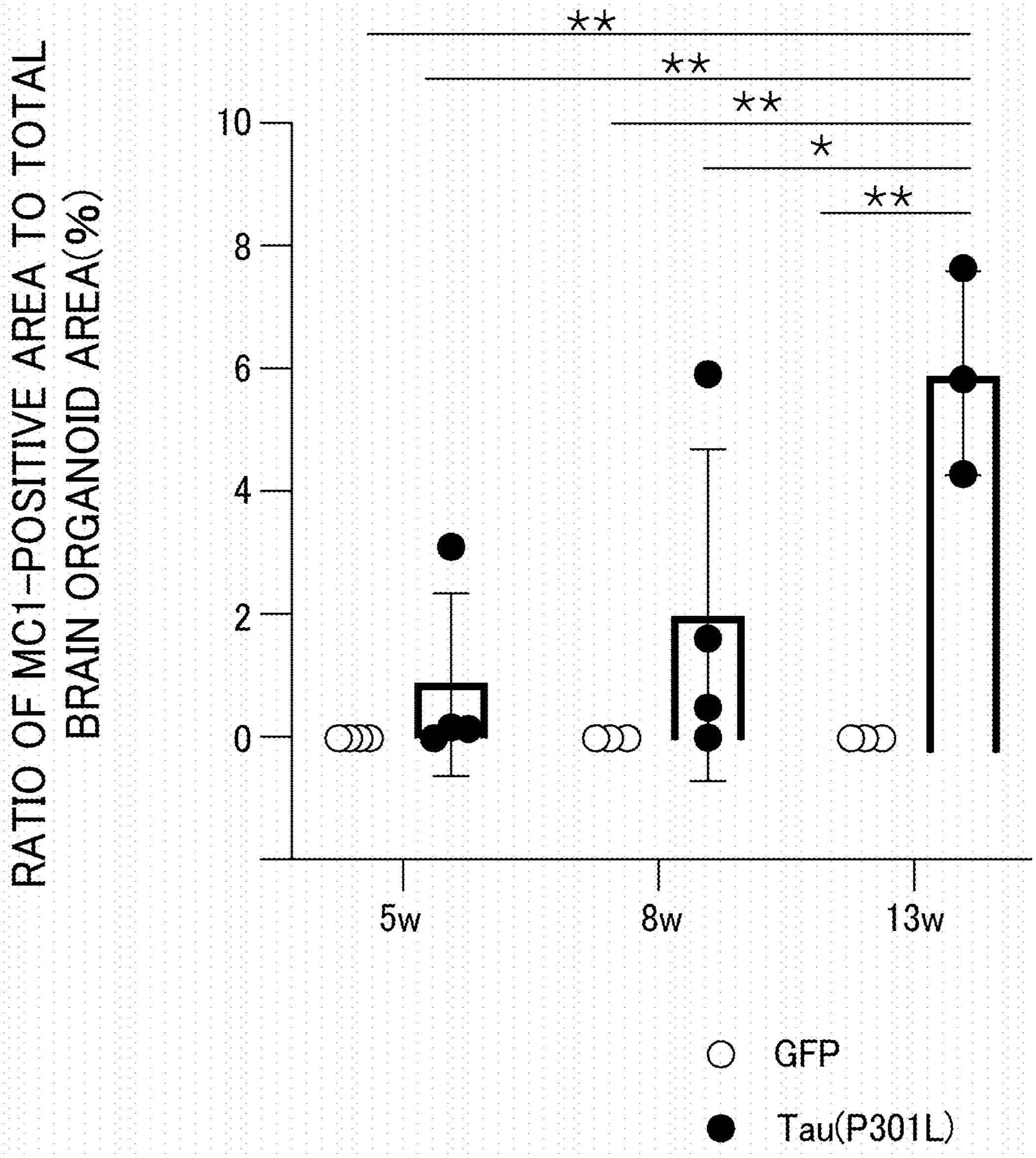
FIG. 9 is a graph showing the quantified results of the results of FIG. 8.

FIG. 8 is a fluorescence microscope photograph showing the results of immunohistochemical staining. In addition, FIG. 9 is a graph showing the quantified results of the results of FIG. 8. In FIG. 8 and FIG. 9, "5w", "8w", and "13w" each indicate the results for injecting virus particles into each brain organoid on days 35 to 41 of culturing (5 weeks), days 56 to 62 of culturing (8 weeks), and days 91 to 97 of culturing (13 weeks). In addition, "GFP" indicates the results for introducing AAV(PHP.B)-CAG-EGFP and "Tau (P301L)" indicates the results for introducing AAV(PHP.B)-CAG-Tau(1N4R)-P301L.

In addition, in FIG. 8, "MC1" indicates the results for staining with an MC1 antibody, "Tau" indicates the results for staining with an anti-tau antibody, "Hoechst" indicates the results for staining the nucleus with Hoechst 33342, and "Merge" indicates the results for merging photographs. In addition, "w/o AAV injection" indicates the results for not injecting AAV virus particles.

In addition, in FIG. 9, the vertical axis indicates the ratio (%) of the area of the region where an aggregated tau protein is present (the region stained with an MC1 antibody) with respect to the total area of the brain organoid cross-section. In addition, the numerical values indicate the average value±standard deviation, "*" indicates that there was a significant difference at P<0.004 and "**" indicates that there was a significant difference at P<0.006.

As a result, it was clear that, in all of the brain organoids from days 35 to 41 of culturing (5 weeks), days 56 to 62 of culturing (8 weeks), and days 91 to 97 of culturing (13 weeks), when AAV(PHP.B)-CAG-Tau(1N4R)-P301L was introduced by injection, the average ratio of the area of the region where an aggregated tau protein was present (the region stained with an MC1 antibody) with respect to the total area of the brain organoid cross-section was 1% or more.

In particular, it was clear that, when AAV(PHP.B)-CAG-Tau(1N4R)-P301L was introduced by injection into brain organoids on days 91 to 97 of culturing (13 weeks), the ratio of the area of the region where an aggregated tau protein was present (the region stained with an MC1 antibody) with respect to the total area of the brain organoid cross-section increased significantly.

This result further supports the possibility of using the brain organoids of the present experimental example as a tau aggregation model.

Experimental Example 3

(Analysis of Brain Organoids having Aggregated Tau Protein 1)

Brain Organoids were Produced by Culturing Pluripotent Stein Cells in the Same manner as in Experimental Example 1. A wild-type human iPS cell line 201B7 was used as the pluripotent stem cells.

The mutant MAPT gene was introduced into brain organoids on days 91 to 97 of culturing (13 weeks). Introduction of the mutant MAPT gene was carried out by injecting the virus particles (AAV(PHP.B)-CAG-Tau(1N4R)-P301L) described above using a gas injector. In addition, for comparison, a group injected with AAV virus particles expressing EGFP (AAV(PHP.B)-CAG-EGFP) instead of the mutant MAPT gene was also prepared.

After that, the suspension-culturing of each brain organoid was continued and each brain organoid was extracted and fixed with 4% paraformaldehyde 5 weeks after the introduction of each of the virus particles. Subsequently, the fixed organoids were then embedded in resin and sections were prepared. In addition, for comparison, sections of brain tissue derived from Alzheimer's disease patients and sections of brain tissue derived from healthy subjects were also prepared.

Subsequently, each section was immunohistochemical stained using thioflavin S and an anti-phosphorylated tau antibody (clone AT8, Fujirebio Inc.) and tau protein aggregation was examined. In addition, the nucleus was stained with Hoechst 33342. Thioflavin S is a compound that specifically binds to the β-sheet structure of protein and emits fluorescence.

Figure 10:
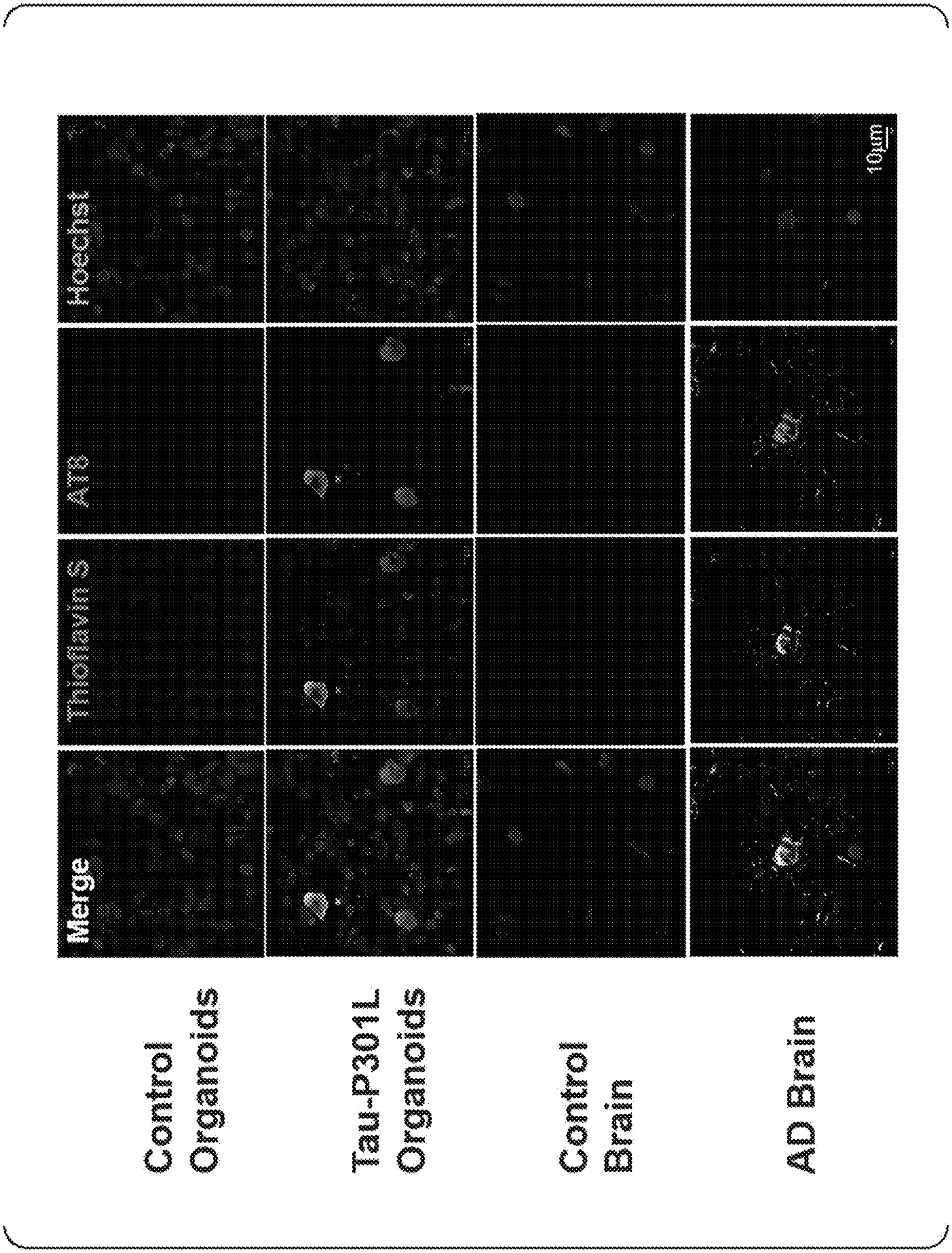
FIG. 10 is a fluorescence microscope photograph showing the results of immunohistochemical staining in Experimental Example 3.

FIG. 10 is a fluorescence microscope photograph showing the results of immunohistochemical staining. In FIG. 10, "Control Organoids" indicates the results for brain organoids to which AAV(PHP.B)-CAG-EGFP was introduced, "Tau-P301L Organoids" indicates the results for brain organoids to which AAV(PHP.B)-CAG-Tau(1N4R)-P301L was introduced, "Control Brain" indicates the results for brain tissue derived from healthy subjects, and "AD Brain" indicates the results for brain tissue derived from Alzheimer's disease patients. In addition, "Thioflavin S" indicates the results for staining with thioflavin S, "AT8" indicates the results for staining with an anti-phosphorylated tau antibody, and "Hoechst" indicates the results for staining the nucleus with Hoechst 33342, and "Merge" indicates the results for merging photographs.

As a result, in brain organoids into which AAV(PHP.B)-CAG-Tau(1N4R)-P301L was introduced, it was clear that, similar to brain tissue derived from Alzheimer's disease patients, regions where β-sheet structures were present (regions stained with thioflavin S) and regions where phosphorylated tau protein was present (regions stained with an AT8 antibody) were detected and also that these stained regions overlapped.

This result indicates that, in brain organoids into which AAV(PHP.B)-CAG-Tau(1N4R)-P301L was introduced, similar to brain tissue derived from Alzheimer's disease patients, aggregates that form β-sheet structures including phosphorylated tau are present.

This result further supports the possibility of using the brain organoids of this experimental example as a tau aggregation model.

Experimental Example 4

(Analysis of Brain Organoids Having Aggregated Tau Protein 2)

Brain organoids were produced by culturing pluripotent stem cells in the same manner as in Experimental Example 1. A wild-type human iPS cell line 201B7 was used as the pluripotent stem cells.

A mutant MAPT gene was introduced into each brain organoid on days 56 to 62 of culturing (8 weeks) and days 91 to 97 of culturing (13 weeks). Introduction of the mutant MAPT gene was carried out by injecting the virus particles (AAV(PHP.B)-CAG-Tau(1N4R)-P301L) described above using a gas injector. In addition, for comparison, a group injected with AAV virus particles expressing EGFP (AAV(PHP.B)-CAG-EGFP) instead of the mutant MAPT gene was also prepared.

After that, the suspension-culturing of each brain organoid was continued and, 5 weeks after the introduction of each of the virus particles, each brain organoid was extracted and homogenized to prepare a sarkosyl-insoluble fraction.

Subsequently, the presence or absence of phosphorylated tau in the prepared sarkosyl-insoluble fraction was analyzed by Western blotting using an anti-tau antibody (clone HT7, Fujirebio Inc.) and an anti-phosphorylated tau antibody (pS396, Thermo Fisher Scientific Inc.). An anti-tau antibody (clone HT7) detects all the tau. In addition, an anti-phosphorylated tau antibody (pS396) detects phosphorylated tau.

Figure 11:
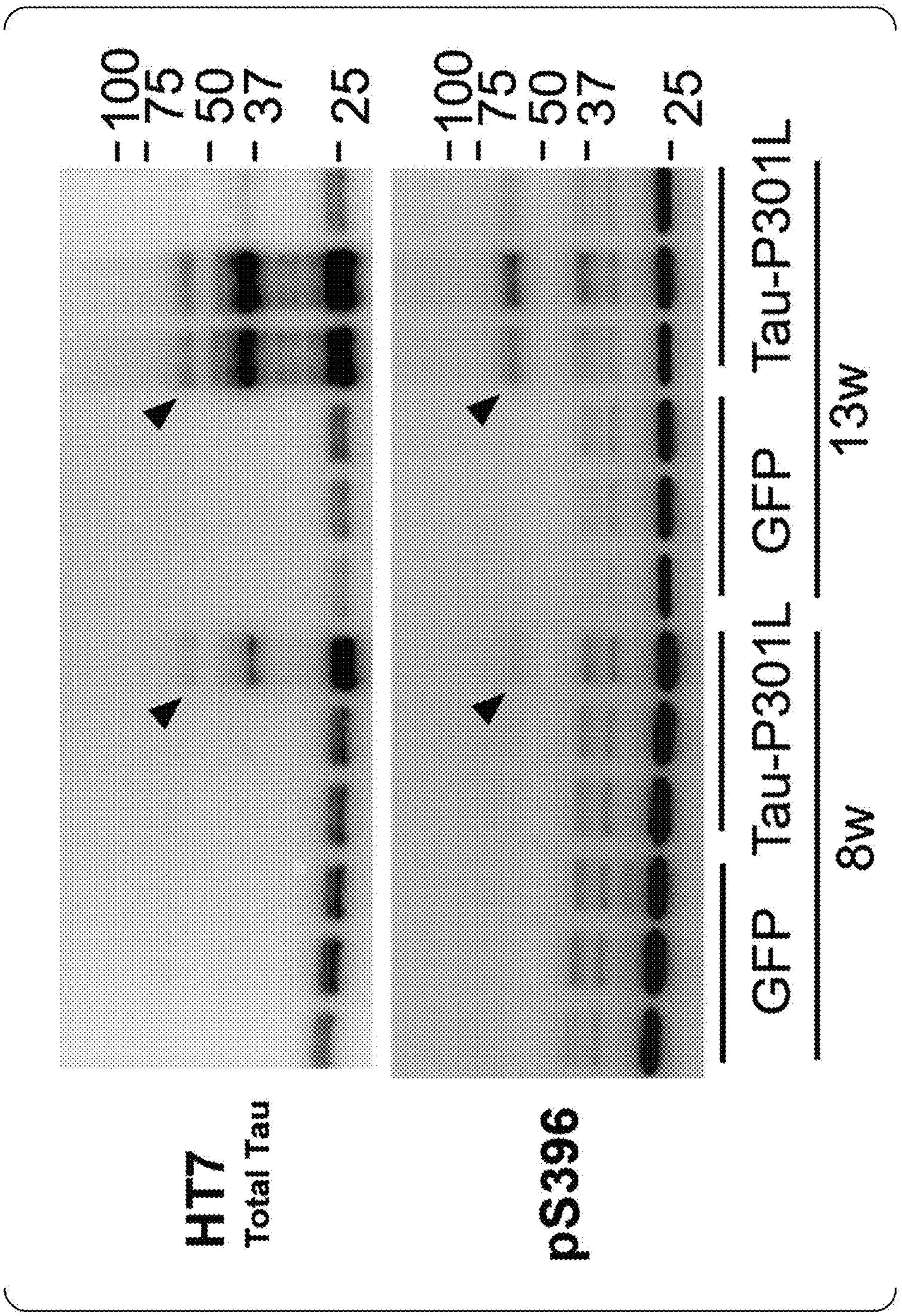
FIG. 11 is a photograph showing the results of Western blotting in Experimental Example 4.
Figure 12:
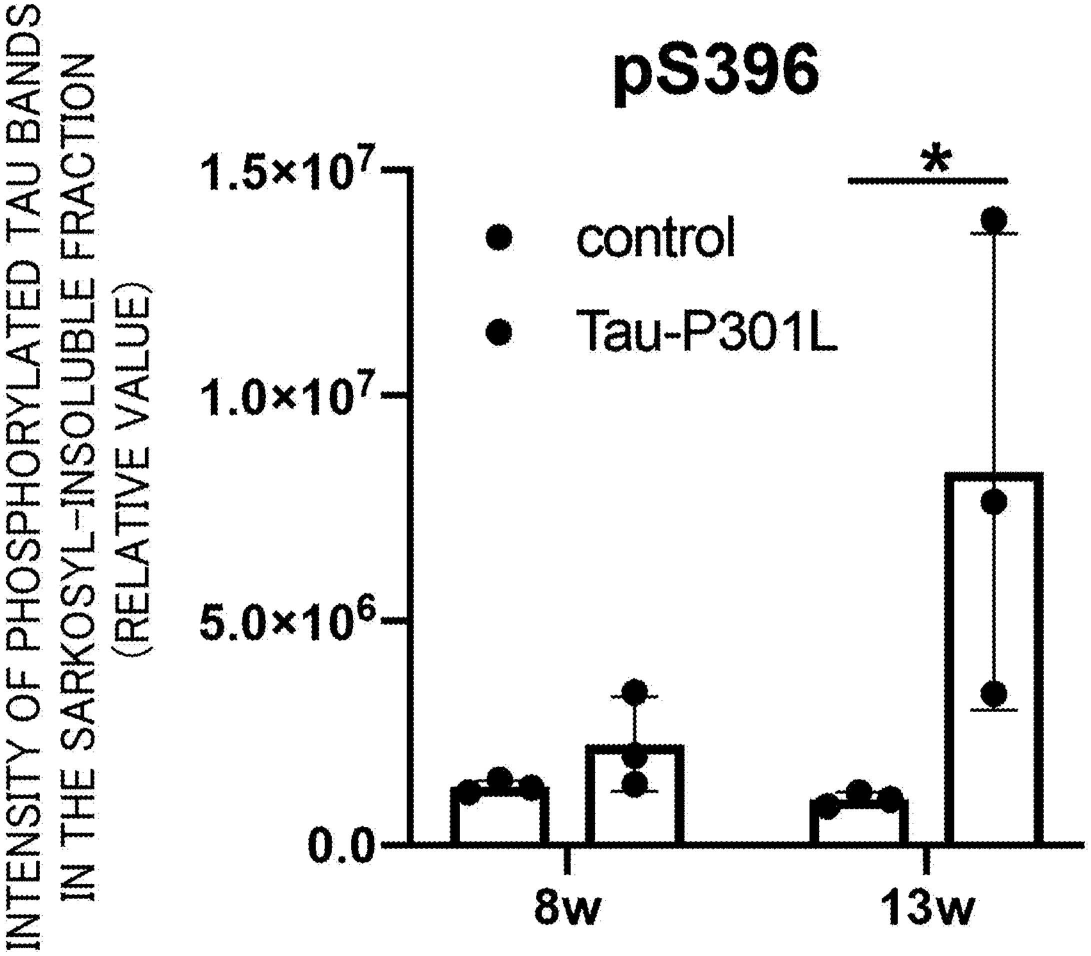
FIG. 12 is a graph showing the quantified results of the results of FIG. 11.

FIG. 11 is a photograph showing the results of Western blotting. In addition, FIG. 12 is a graph showing the quantified results of the results of FIG. 11. In FIG. 11 and FIG. 12, "8w" and "13w" indicate the results for injecting virus particles into each brain organoid on each of days 56 to 62 of culturing (8 weeks) and days 91 to 97 of culturing (13 weeks).

In FIG. 11, "GFP" indicates the results for introducing AAV(PHP.B)-CAG-EGFP and "Tau(P301L)" indicates the results for introducing AAV(PHP.B)-CAG-Tau(1N4R)-P301L. In addition, in FIG. 11, "HT7" indicates the results for staining with an anti-tau antibody and "pS396" indicates the results for staining with an anti-phosphorylated tau antibody. In addition, arrowheads indicate tau and phosphorylated tau bands.

In FIG. 12, "control" indicates the results for introducing AAV(PHP.B)-CAG-EGFP and "Tau-P301L" indicates the results for introducing AAV(PHP.B)-CAG-Tau(1N4R)-P301L. The vertical axis in FIG. 12 indicates the intensity (relative value) of the phosphorylated tau band in the sarkosyl-insoluble fraction. In addition, "*" indicates that there was a significant difference at p<0.05.

As a result, it was clear that in brain organoids to which AAV(PHP.B)-CAG-Tau(1N4R)-P301L was introduced, phosphorylated tau was present in the sarkosyl-insoluble fraction. In particular, it was clear that, when AAV(PHP.B)-CAG-Tau(1N4R)-P301L was introduced into brain organoids at days 91 to 97 of culturing (13 weeks), the amount of phosphorylated tau present in the sarkosyl-insoluble fraction significantly increased.

This result further supports the possibility of using the brain organoids of this experimental example as a tau aggregation model.

Experimental Example 5

(Analysis of Brain Organoids Having Aggregated Tau Protein 3)

Brain organoids were produced by culturing pluripotent stein cells in the same manner as in Experimental Example 1. A wild-type human iPS cell line 201B7 was used as the pluripotent stem cells.

The mutant MAPT gene was introduced into brain organoids on days 91 to 97 of culturing (13 weeks). Introduction of the mutant MAPT gene was carried out by injecting the virus particles (AAV(PHP.B)-CAG-Tau(1N4R)-P301L) described above using a gas injector. In addition, for comparison, a group injected with AAV virus particles expressing EGFP (AAV(PHP.B)-CAG-EGFP) instead of the mutant MAPT gene was also prepared.

Figure 13:
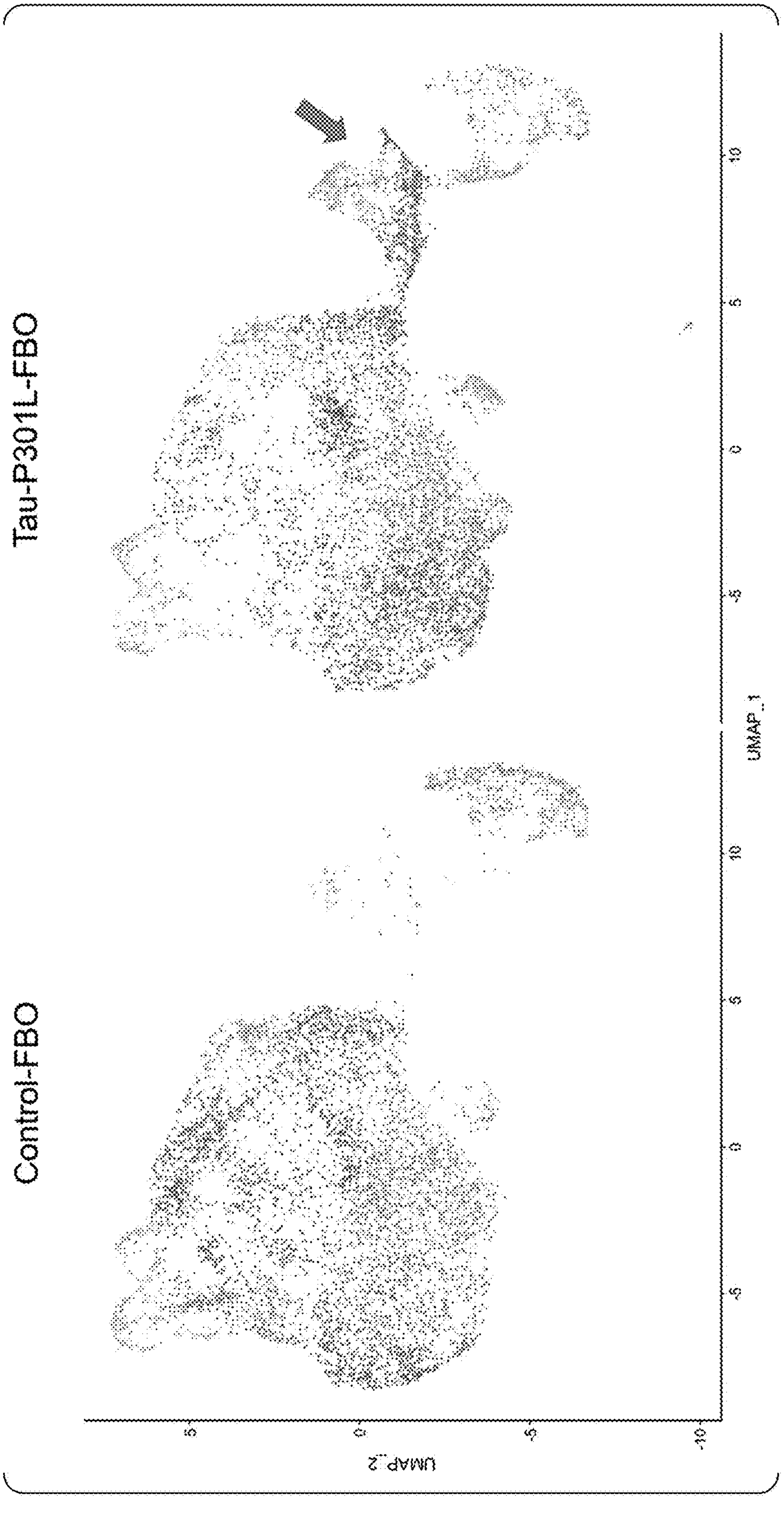
FIG. 13 is a graph in which gene expression is analyzed based on the results of RNA-seq analysis in Experimental Example 5 and in which clustering results are plotted in a two-dimensional form using UMAP.

After that, the suspension-culturing of each brain organoid was continued and, 5 weeks after the introduction of each of the virus particles, each brain organoid was extracted and subjected to single-cell RNA-seq analysis. FIG. 13 is a graph in which clustering results analyzing gene expression based on the results of the RNA-seq analysis are two-dimensionally plotted using UMAP.

In FIG. 13, "Control-FBO" indicates the results for brain organoids to which AAV(PHP.B)-CAG-EGFP was introduced and "Tau-P301L-FBO" indicates the results for brain organoids to which AAV(PHP.B)-CAG-Tau(1N4R)-P301L was introduced. As a result, it was clear that, in Tau-P301L-FBO, a cluster, which is not present in Control-FBO, is present at the position indicated by the arrow in FIG. 13.

Figure 14:
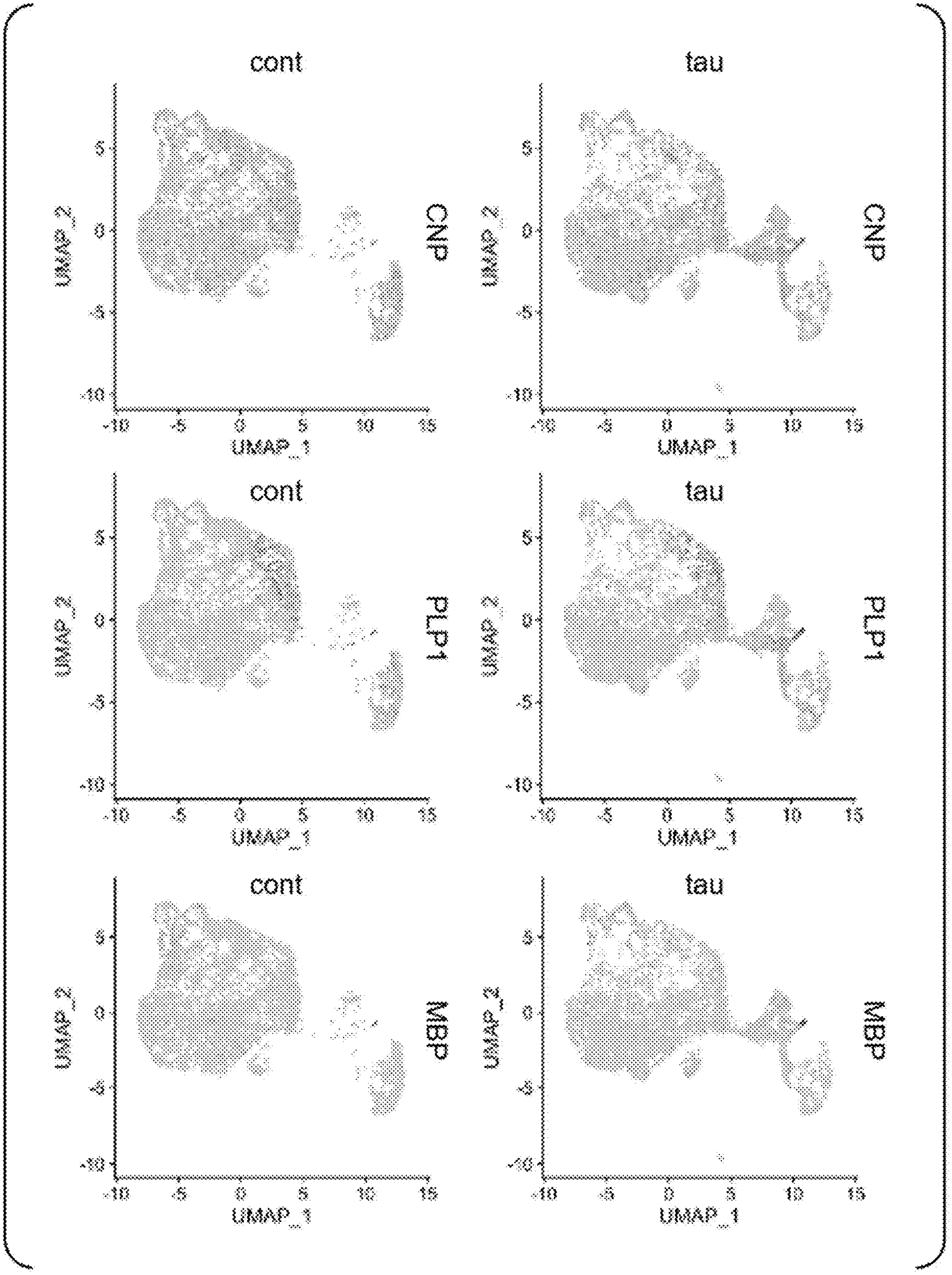
FIG. 14 is a graph showing the results of expression analysis of the CNP gene, PLP1 gene, and MBP gene in Experimental Example 5.
Figure 15:
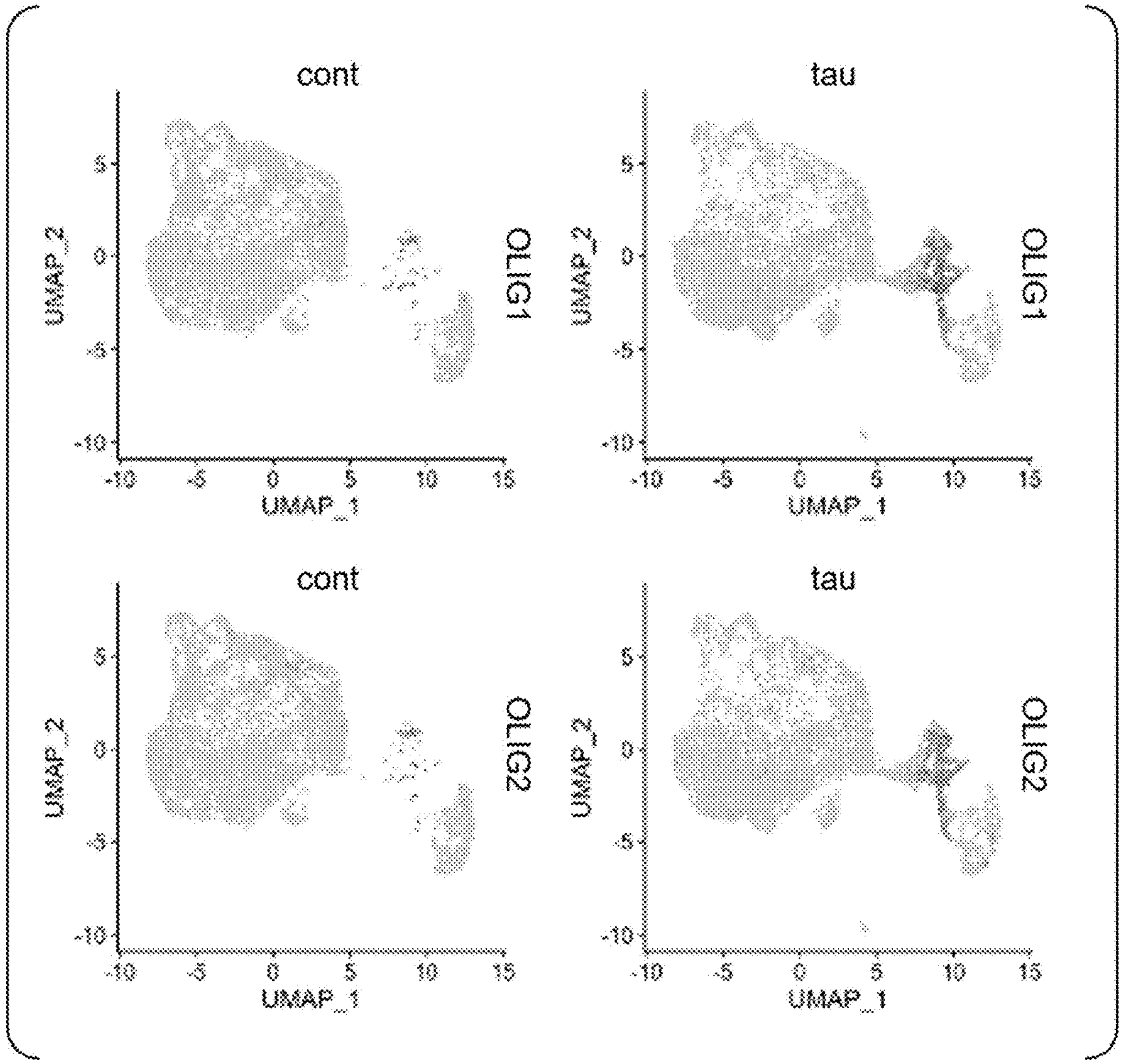
FIG. 15 is a graph showing the results of expression analysis of the OLIG1 gene and OLIG2 gene in Experimental Example 5.
Figure 16:
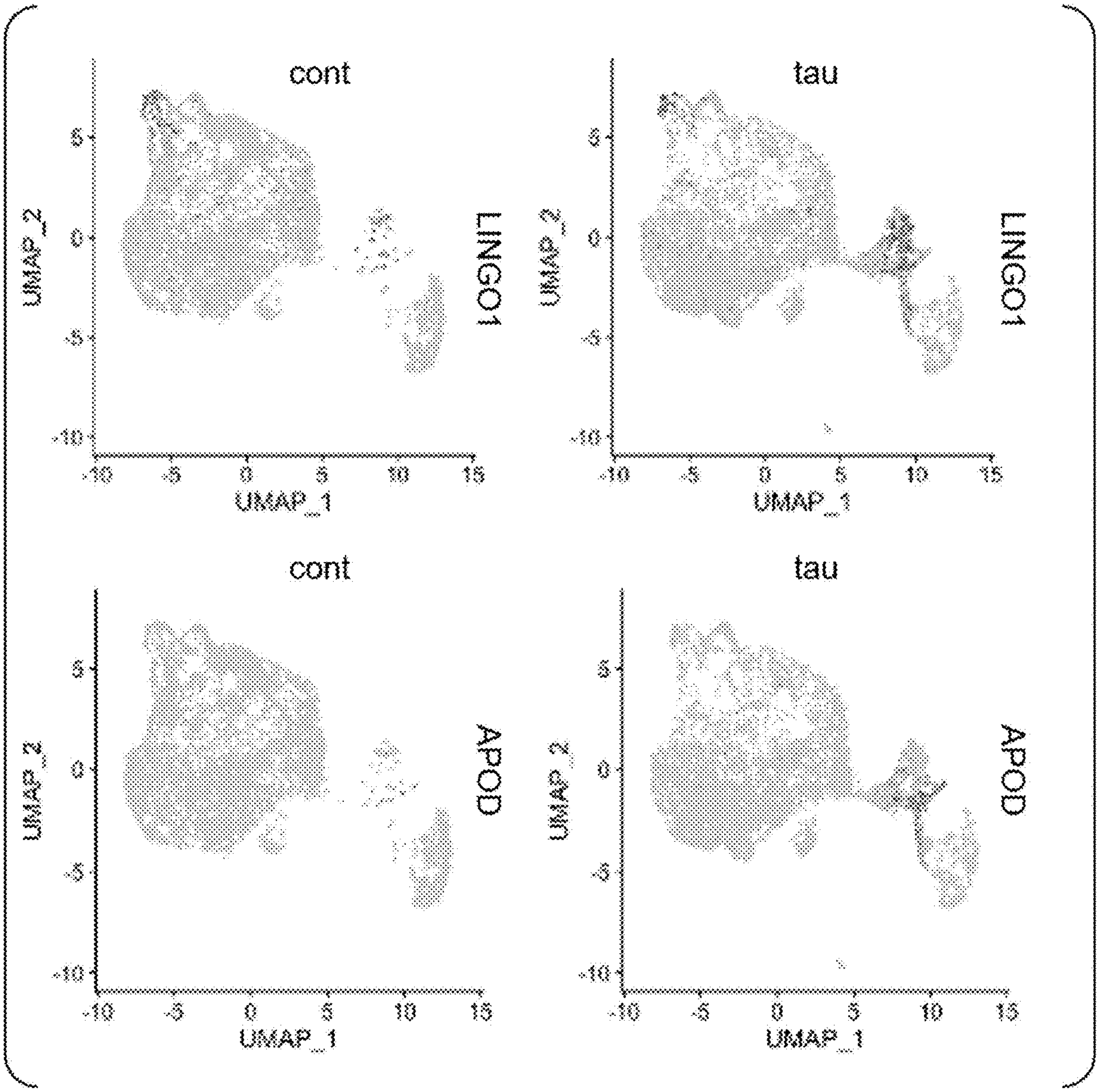
FIG. 16 is a graph showing the results of expression analysis of the LINGO1 gene and APOD gene in Experimental Example 5.

FIG. 14 to FIG. 16 are graphs showing the results of expression analysis of each gene shown in the figures. A search was carried out in published papers, genes expressed in clusters of neurons that are present only in patients with Alzheimer's disease were extracted, and the expression of those genes was analyzed.

In FIG. 14 to FIG. 16, "cont" indicates the results for brain organoids to which AAV(PHP.B)-CAG-EGFP was introduced and "tau" indicates the results for brain organoids to which AAV(PHP.B)-CAG-Tau(1N4R)-P301L was introduced.

As a result, it was clear that the expression of genes such as LINGO1, OLIG1, OLIG2, and CNPase (CNP) was increased in the clusters that appeared in Tau-P301L-FBO.

Subsequently, the expression and localization of CNP at the protein level were analyzed by immunohistochemical staining. Control-FBO and Tau-P301L-FBO were fixed with 4% paraformaldehyde. Subsequently, the fixed organoids were then embedded in resin and sections were prepared. In addition, for comparison, sections of brain tissue derived from Alzheimer's disease patients and sections of brain tissue derived from healthy subjects were also prepared.

Subsequently, each section was immunostained using each of an anti-CNPase antibody, an anti-tau antibody (RTM38, Fujifilm Wako Pure Chemical Industries, Ltd.), and an anti-HuC/HuD antibody. In addition, the nucleus was stained with Hoechst 33342.

Figure 17:
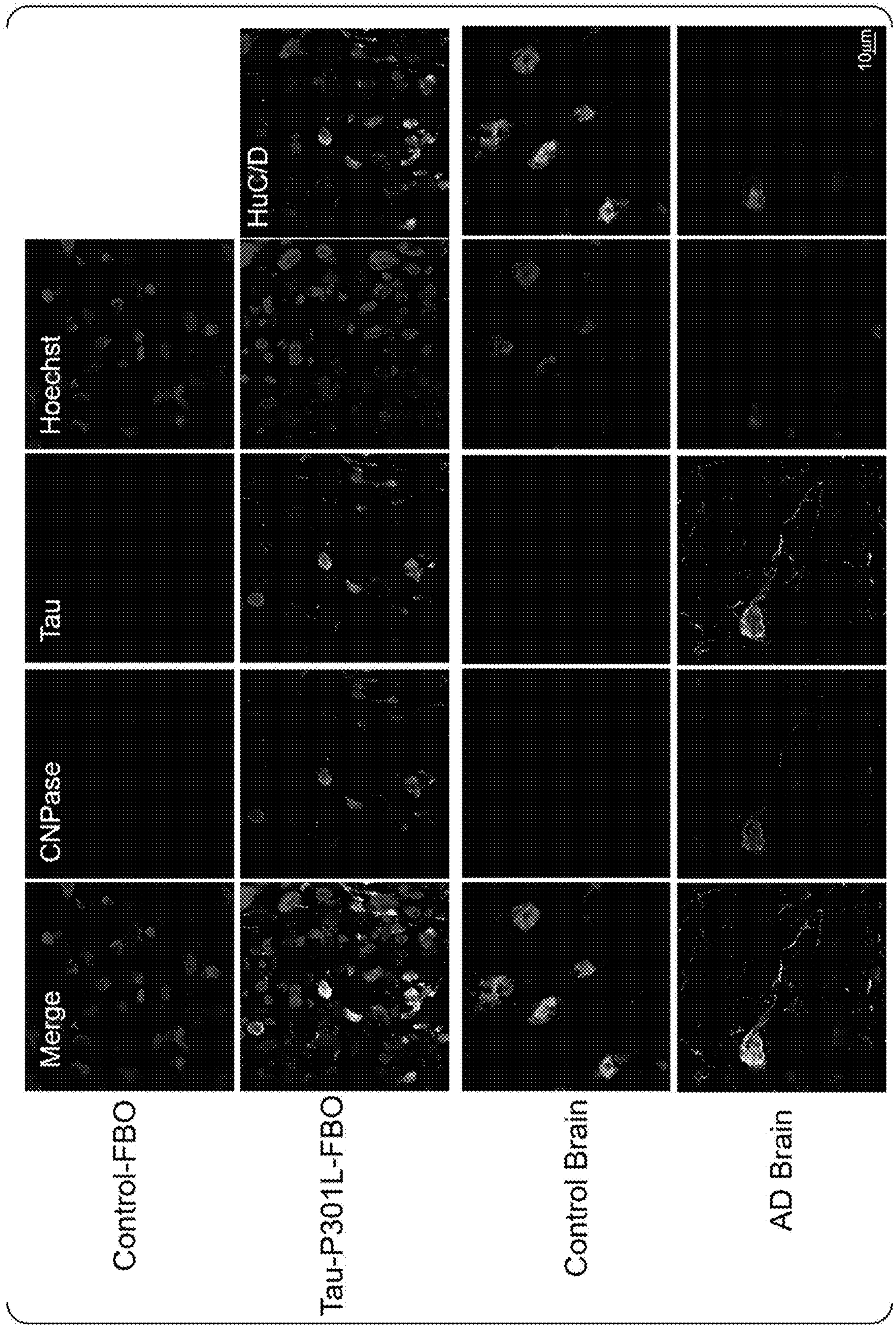
FIG. 17 is a fluorescence microscope photograph showing the results of immunohistochemical staining in Experimental Example 5.

FIG. 17 is a fluorescence microscope photograph showing the results of immunohistochemical staining. In FIG. 17, "Control-FBO" indicates the results for brain organoids to which AAV(PHP.B)-CAG-EGFP was introduced, "Tau-P301L-FBO" indicates the results for brain organoids to which AAV(PHP.B)-CAG-Tau(1N4R)-P301L was introduced, "Control Brain" indicates the results for brain tissue derived from healthy subjects, and "AD Brain" indicates the results for brain tissue derived from Alzheimer's disease patients. In addition, "CNPase" indicates the results for staining with an anti-CNPase antibody, "Tau" indicates the results for staining with an anti-tau antibody, "Hoechst" indicates the results for staining the nucleus with Hoechst 33342, "HuC/D" indicates the results for staining with an anti-HuC/HuD antibody, and "Merge" indicates the results for merging photographs.

As a result, it was confirmed that tau protein and CNPase co-localized in brain organoids to which AAV(PHP.B)-CAG-Tau(1N4R)-P301L was introduced. In addition, it was confirmed that tau protein and CNPase are also co-localized in brain tissue derived from Alzheimer's disease patients.

This result further supports the possibility of using the brain organoids of this experimental example as a tau aggregation model.

INDUSTRIAL APPLICABILITY

According to the present invention, it is possible to provide a technique for efficiently producing a brain organoid having an aggregated tau protein.

The invention claimed is:

1. A method for producing a brain organoid having an aggregated tau protein, the method comprising:

(a) culturing pluripotent stem cells in a presence of a SMAD inhibitor to form an embryoid body;

(b) embedding the embryoid body in an extracellular matrix and three-dimensionally culturing the embryoid body in a presence of a SMAD inhibitor and a glycogen synthase kinase 3P (GSK3P) inhibitor to form an organoid that includes neural precursor cells;

(c) extracting the organoid from the extracellular matrix and suspension-culturing the organoid in a presence of leukemia inhibitory factor (LIF) to form a brain organoid;

(d) forcing the brain organoid to express a mutant microtubule associated protein tau (MAPT) gene; and (e) further suspension-culturing the brain organoid after the (d) to obtain a brain organoid having an aggregated tau protein, wherein the brain organoid comprises a cross-section with an average ratio of an area of a region where a phosphorylated tau protein is present is 2% or more with respect to a total area of the cross-section, or, in a cross-section, an average ratio of an area of a region where an aggregated tau protein is present is 1% or more with respect to a total area of the cross-section.

2. The method for producing a brain organoid according to claim 1, wherein the mutant MAPT gene is a gene encoding a tau protein having a P301L mutation.

3. The method for producing a brain organoid according to claim 1, wherein forced expression of the mutant MAPT gene is performed by gene transfer using an adeno-associated virus (AAV).

4. The method for producing a brain organoid according to claim 3, wherein the forced expression of the mutant MAPT gene is performed by injecting the AAV into the brain organoid.

5. The method for producing according to claim 1, wherein at least a part of the (c) is performed in a presence of more than 20% by volume of oxygen.

6. The method for producing according to claim 1, wherein the (c) is performed for 3 weeks or longer.

7. The method for producing according to claim 1, wherein the step (e) is performed for 5 weeks or longer.

8. The method for producing according to claim 1, further comprising:

culturing the pluripotent stem cells in a presence of less than 100 ng/ml of fibroblast growth factor-2 (FGF2) before the (a).

9. The method for producing according to claim 1, wherein the pluripotent stem cells are cultured feeder-free.

10. A brain organoid produced according to the method of claim 1, wherein the brain organoid comprises a cross-section with an average ratio of an area of a region where a phosphorylated tau protein is present is 2% or more with respect to a total area of the cross-section, or, in a cross-section, an average ratio of an area of a region where an aggregated tau protein is present is 1% or more with respect to a total area of the cross-section.

* * * * *